(12) United States Patent
Morino et al.

(10) Patent No.: US 11,444,324 B2
(45) Date of Patent: Sep. 13, 2022

(54) ELECTROLYTE FOR SECONDARY BATTERY, SECONDARY BATTERY, BATTERY PACK, ELECTRIC VEHICLE, ELECTRIC POWER STORAGE SYSTEM, ELECTRIC TOOL AND ELECTRONIC DEVICE

(71) Applicant: MURATA MANUFACTURING CO., LTD., Kyoto (JP)

(72) Inventors: Yusuke Morino, Kyoto (JP); Izaya Okae, Kyoto (JP); Nobuhiro Inoue, Kyoto (JP); Kazumasa Takeshi, Kyoto (JP)

(73) Assignee: Murata Manufacturing Co., Ltd., Kyoto (JP)

(*) Notice: Subject to any disclaimer, the term of this patent is extended or adjusted under 35 U.S.C. 154(b) by 197 days.

(21) Appl. No.: 16/534,690

(22) Filed: Aug. 7, 2019

(65) Prior Publication Data

US 2020/0058959 A1 Feb. 20, 2020

Related U.S. Application Data

(63) Continuation of application No. PCT/JP2017/036995, filed on Oct. 12, 2017.

(30) Foreign Application Priority Data

Feb. 8, 2017 (JP) .............................. JP2017-021046

(51) Int. Cl.
*H01M 10/0525* (2010.01)
*H01M 10/0567* (2010.01)
(Continued)

(52) U.S. Cl.
CPC ....... *H01M 10/0567* (2013.01); *C07C 317/08* (2013.01); *C07C 317/10* (2013.01);
(Continued)

(58) Field of Classification Search
CPC ......... H01M 10/0567; H01M 10/0569; H01M 10/0568; H01M 10/0525; H01M 2300/0028
See application file for complete search history.

(56) References Cited

U.S. PATENT DOCUMENTS

| 2012/0301797 A1* | 11/2012 | Abe ................. H01M 10/0567 429/188 |
| 2013/0089778 A1* | 4/2013 | Ihara ................. H01M 10/0567 429/200 |

(Continued)

FOREIGN PATENT DOCUMENTS

| CN | 102696142 | 9/2012 |
| CN | 104823319 | 8/2015 |

(Continued)

OTHER PUBLICATIONS

Japanese Office Action dated Jun. 9, 2020 in corresponding Japanese Application No. 2017-021046.

(Continued)

*Primary Examiner* — Osei K Amponsah
(74) *Attorney, Agent, or Firm* — K&L Gates LLP

(57) ABSTRACT

A secondary battery includes a positive electrode, a negative electrode, and an electrolytic solution where (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds.

15 Claims, 4 Drawing Sheets

(51) Int. Cl.
*C07C 317/08* (2006.01)
*C07C 317/10* (2006.01)
*C07C 317/12* (2006.01)
*C07D 275/02* (2006.01)
*C07D 275/06* (2006.01)
*H01M 10/0568* (2010.01)
*H01M 10/0569* (2010.01)

(52) U.S. Cl.
CPC .......... *C07C 317/12* (2013.01); *C07D 275/02* (2013.01); *C07D 275/06* (2013.01); *H01M 10/0525* (2013.01); *H01M 10/0568* (2013.01); *H01M 10/0569* (2013.01); *H01M 2300/0028* (2013.01)

(56) References Cited

U.S. PATENT DOCUMENTS

| | | | |
|---|---|---|---|
| 2015/0064549 | A1 | 3/2015 | Pinnell et al. |
| 2016/0028115 | A1* | 1/2016 | Kim .................. H01M 10/0569 429/338 |
| 2016/0240858 | A1* | 8/2016 | Yamada ............ H01M 10/0525 |
| 2017/0117582 | A1 | 4/2017 | Mizuno et al. |

FOREIGN PATENT DOCUMENTS

| | | |
|---|---|---|
| JP | 2003-157832 | 5/2003 |
| JP | 2006-286606 | 10/2006 |
| JP | 2011238373 A | 11/2011 |
| JP | 2014007010 A | 1/2014 |
| JP | 2014-192153 | 10/2014 |
| JP | 2015179672 A | 10/2015 |
| JP | 2016503571 A | 2/2016 |
| JP | 2016105394 A | 6/2016 |
| JP | 2016-167437 | 9/2016 |
| JP | 2016167446 A | 9/2016 |
| JP | 2016192405 A | 11/2016 |
| JP | 2017027930 A | 2/2017 |
| WO | 2015037367 A1 | 3/2015 |

OTHER PUBLICATIONS

International Search Report for Application No. PCT/JP2017/036995, dated Jan. 9, 2018.
Japanese Office Action dated Feb. 9, 2021 in corresponding Japanese Application No. 2017-021046.
Chinese Office Action dated Dec. 23, 2021 in corresponding Chinese Application No. 201780085903.6.

* cited by examiner

ELECTROLYTE FOR SECONDARY BATTERY, SECONDARY BATTERY, BATTERY PACK, ELECTRIC VEHICLE, ELECTRIC POWER STORAGE SYSTEM, ELECTRIC TOOL AND ELECTRONIC DEVICE

CROSS-REFERENCE TO RELATED APPLICATIONS

The present application is a continuation of PCT patent application no. PCT/JP2017/036995, filed on Oct. 12, 2017, which claims priority to Japanese Application No. 2017-021046, filed Feb. 8, 2017, the entire contents of which are incorporated herein by reference.

TECHNICAL FIELD

The present technology relates to an electrolytic solution that is used for a secondary battery, a secondary battery including the electrolytic solution, and a battery pack, an electric vehicle, a power storage system, a power tool, and an electronic device, which include the secondary battery.

BACKGROUND ART

Various electronic devices such as mobile phones and personal digital assistants (PDA) have been widely used, and it has been demanded to further reduce size and weight of the electronic devices and to achieve their longer lives. Therefore, the development of batteries, in particular, small-size and light-weight secondary batteries capable of acquiring a high energy density has been advanced as power supplies.

The secondary batteries are considered to be applied not only to the electronic devices mentioned above, but also to other uses. An example of the other uses is a battery pack that is detachably mounted on an electronic device or the like, an electric vehicle such as an electric car, a power storage system such as a home electric power server, and a power tool such as an electric drill.

The secondary battery includes an electrolytic solution together with a positive electrode and a negative electrode. The composition of the electrolytic solution greatly affects the battery characteristics, and various studies have been thus made regarding the composition of the electrolytic solution.

Specifically, in order to suppress a decomposition reaction of an electrolytic solution, the electrolytic solution contains 1,3-propene sultone, 2-sulfobenzoic anhydride, methyl-2-propynyl sulfite, and the like (for example, see Patent Documents 1 to 3).

PRIOR ART DOCUMENT

Patent Documents

Patent Document 1: U.S. Pat. No. 4,190,162
Patent Document 2: U.S. Pat. No. 4,557,381
Patent Document 3: U.S. Pat. No. 3,823,712

SUMMARY OF THE INVENTION

The electronic devices and the like have been more and more increased in performance and function. For this reason, the frequency of use of electronic devices and the like has been increased, and the usage environment for the electronic devices and the like has been expanded. Therefore, there is still room for improvement regarding the battery characteristics of the secondary batteries.

Accordingly, it is desirable to provide an electrolytic solution for a secondary battery, a secondary battery, a battery pack, an electric vehicle, a power storage system, a power tool, and an electronic device, which are capable of acquiring excellent battery characteristics.

An electrolytic solution for a secondary battery according to an embodiment of the present technology is an electrolytic solution in which (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3).

[Chem. 1]

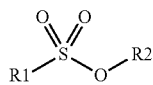
(1)

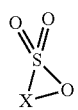
(2)

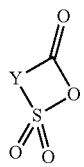
(3)

(where each of R1 and R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, provided that at least one of R1 and R2 is any one of the monovalent unsaturated hydrocarbon group and the monovalent binding group, and each of X and Y is a divalent unsaturated hydrocarbon group.)

A secondary battery according to an embodiment of the present technology includes a positive electrode, a negative electrode, and an electrolytic solution, and the electrolytic solution has a configuration similar to that of the electrolytic solution for a secondary battery according to the embodiment of the present technology as mentioned above.

Each of a battery pack, an electric vehicle, a power storage system, a power tool, and an electronic device according to an embodiment of the present technology includes a secondary battery, and the secondary battery has a configuration similar to that of the secondary battery according to the embodiment of the present technology as described above.

Here, the "monovalent saturated hydrocarbon group" is a generic term for a monovalent group which is constituted of carbon (C) and hydrogen (H) and does not contain an unsaturated carbon bond. The "monovalent unsaturated hydrocarbon group" is a generic term for a monovalent group which is constituted of carbon and hydrogen and contains one or two or more unsaturated carbon bonds. The "divalent unsaturated hydrocarbon group" is a generic term for a divalent group which is constituted of carbon and hydrogen and contains one or two or more unsaturated carbon bonds. The unsaturated carbon bond is a carbon-carbon double bond (>C=C<) and a carbon-carbon triple bond (—C≡C—). Each of the monovalent saturated hydrocarbon group, the monovalent unsaturated hydrocarbon group, and the divalent unsaturated hydrocarbon group may have a straight-chain structure, a branched structure with one or two or more side chains, or a cyclic structure.

A molar ratio M2/M1 is a value obtained by rounding off the value of the second decimal place.

In the electrolytic solution for a secondary battery or the secondary battery according to the embodiment of the present technology, the electrolytic solution simultaneously satisfies the conditions shown in (A) to (E), so that it is possible to achieve excellent battery characteristics. Further, in the battery pack, the electric vehicle, the power storage system, the power tool or the electronic device according to the embodiment of the present technology, similar effects are achievable.

It is to be noted that the effects described herein are not necessarily limited, and may be any of the effects described in the present technology.

MODE FOR CARRYING OUT THE INVENTION

Figure 1:
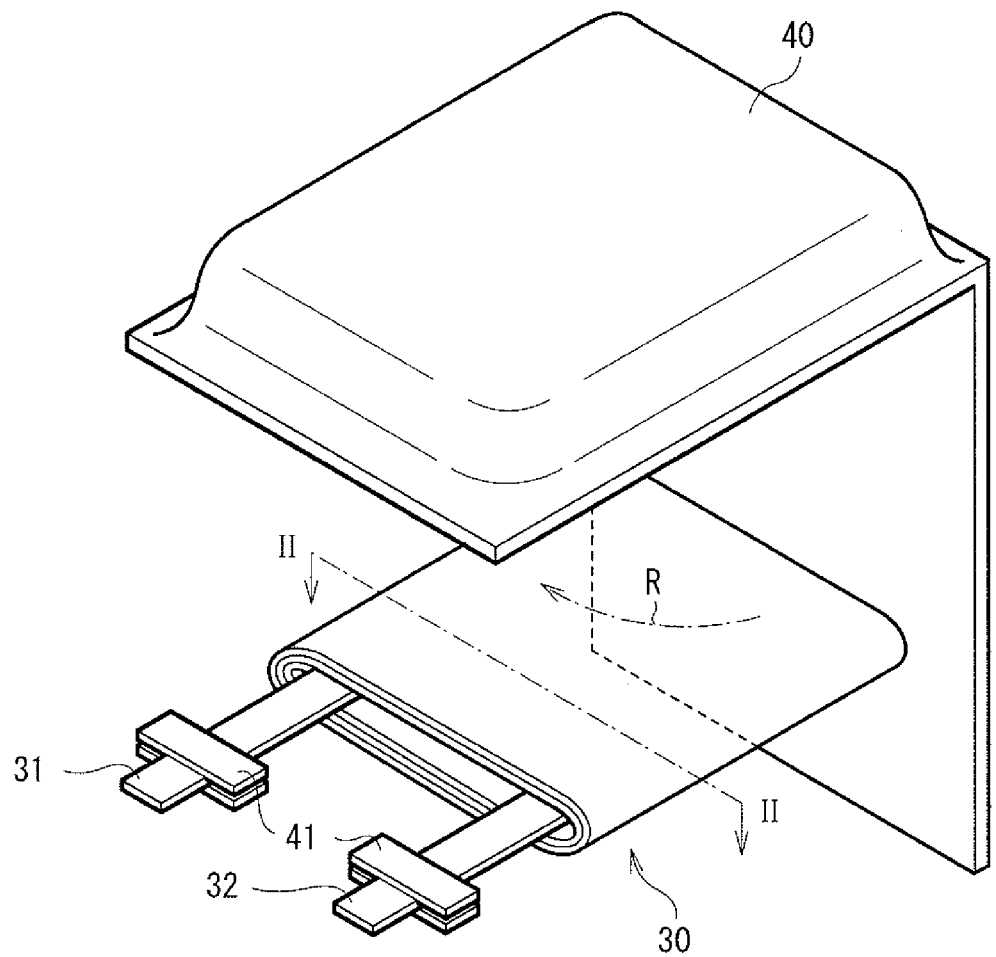
FIG. 1 is a perspective view illustrating a configuration of a secondary battery (laminated film type) according to an embodiment of the present technology.

An embodiment of the present technology will be described in detail below with reference to the drawings. The order of the description is as follows.
1. Electrolytic Solution for Secondary Battery
2. Secondary Battery
3. Application of Secondary Battery
3-1. Battery Pack (Unit Cell)
3-2. Battery Pack (Assembled Battery)
3-3. Electric Vehicle
3-4. Power Storage System
3-5. Power Tool <1. Electrolytic Solution for Secondary Battery>

Firstly, an electrolytic solution for a secondary battery according to an embodiment of the present technology will be described.

The electrolytic solution for a secondary battery (hereinafter simply referred to as "electrolytic solution") described herein is used in, for example, a secondary battery such as a lithium ion secondary battery. However, the kind of the secondary battery in which the electrolytic solution is used is not limited to the lithium ion secondary battery.

[Overall Structure]

The electrolytic solution contains a solvent and an electrolyte salt. The electrolyte salt may be dissolved or dispersed in the solvent.

The solvent contains ethylene carbonate which is a cyclic carbonate ester to be described later and a sulfone compound to be described later. The solvent may contain any one of, or two or more of other materials together with ethylene carbonate and a sulfone compound. Details of the "other materials" will be described later. The electrolytic solution containing ethylene carbonate as a nonaqueous solvent (an organic solvent) is a so-called nonaqueous electrolytic solution.

The kind of the electrolyte salt is not particularly limited. The electrolyte salt may be only one kind or two kinds or more. In particular, the electrolyte salt is preferably a metal salt containing, as a constituent element, a metal element that is the same kind as an electrode reactant. This is because the electrode reaction is easily advanced.

The "electrode reactant" is a substance used for advancing an electrode reaction (charge and discharge reaction) in a secondary battery in which an electrolytic solution is used. For example, an electrode reactant used in a lithium ion secondary battery or the like is lithium. Along with this, in a case where the electrolytic solution is used in, for example, the lithium ion secondary battery in which lithium is used as the electrode reactant, the electrolyte salt is preferably a lithium salt.

[Mixing Ratio of Electrolyte Salt and Ethylene Carbonate]

In the electrolytic solution, the mixing ratio of electrolyte salt and ethylene carbonate is optimized in order to suppress the generation of gas (mainly carbon dioxide) resulting from the decomposition reaction of the electrolytic solution (mainly ethylene carbonate) while sufficiently advancing the electrode reaction using the electrolyte salt.

Specifically, a content (a so-called concentration: mol/kg) of the electrolyte salt in the electrolytic solution, a content (a so-called solvent composition ratio:wt %) of ethylene carbonate in the solvent, and a ratio M2/M1 of a number M2 of moles of ethylene carbonate to a number M1 of moles of the electrolyte salt (a so-called molar ratio) satisfy the following three conditions simultaneously.

Firstly, the molar ratio M2/M1 is 2.4 or less, and preferably from 0.4 to 2.4.

Secondly, the content of the electrolyte salt in the electrolytic solution (mol/kg) is from 0.8 mol/kg to 2.0 mol/kg both inclusive, and preferably from 0.9 mol/kg to 1.5 mol/kg both inclusive. In other words, the content (wt %) of the electrolyte salt in the electrolytic solution is from 12 wt % to 30 wt % both inclusive, and preferably from 14 wt % to 23 wt % both inclusive.

Thirdly, the content (wt %) of ethylene carbonate in the solvent is from 10 wt % to 30 wt % both inclusive.

The reason why the above three conditions are simultaneously satisfied is that, as described above, at the time of using (charging and discharging) the secondary battery in which the electrolytic solution is used, the generation of the gas resulting from the decomposition reaction of the electrolytic solution is suppressed while sufficiently advancing the electrode reaction (charge and discharge reaction) using the electrolyte salt. As a result, even if the secondary battery is repeatedly used, the discharged capacity is less likely to decrease and the secondary battery is less likely to swell.

In particular, since the laminated film type secondary battery (see FIG. 1) described later is produced using a film-like exterior member 40 that is easily deformed in response to an external force, the laminated film type secondary battery tends to swell due to the generation of gas (increase in internal pressure). Therefore, when the above three conditions are simultaneously satisfied with respect to the electrolytic solution used in the laminated film type secondary battery, it effectively makes the secondary battery less likely to swell even if the secondary battery is likely to swell inherently.

In order to suppress the generation of gas resulting from the decomposition reaction of the electrolytic solution, the reason for focusing on one component (ethylene carbonate) of the solvent is that ethylene carbonate has a great influence on the generation of gas.

In detail, in a case where the electrolytic solution is used for the secondary battery, a plurality of factors can be considered as a factor which causes generation of gas at the time of using (at the time of charging and discharging) the secondary battery. In particular, the main factor among the gas generation factors is the decomposition reaction of the solvent, and it is particularly the oxidative decomposition reaction of ethylene carbonate. Since ethylene carbonate plays a role as a high dielectric constant solvent for dissolving the electrolyte salt, and also plays a role in forming a stable film (solid electrolyte interphase (SEI)) on the surface of the negative electrode at the first use of the secondary battery, it is widely used as a solvent for an electrolytic solution. However, ethylene carbonate plays a useful role as described above, but it becomes a major source of gas generation depending on the compatibility with the material of parts (for example, the positive electrode) mounted on the secondary battery as well as charge and discharge conditions. Therefore, as described above, it is necessary to focus attention on ethylene carbonate, which is one component of the solvent, in order to suppress the generation of gas during use of the secondary battery while utilizing the advantage based on the useful role of ethylene carbonate.

Further, it is considered that the reason why the secondary battery is less likely to swell when the above three conditions are simultaneously satisfied is that ethylene carbonate is sufficiently solvated with a cation constituting the electrolyte salt in the electrolytic solution, and thus the electronic state of ethylene carbonate is an electronic state which is less likely to be decarboxylated. The "cation" is, for example, a lithium ion in a case where the electrolyte salt is a lithium salt.

Here, the procedure for specifying the content (mol/kg) of the electrolyte salt in the electrolytic solution is, for example, as follows. In order to specify the content of the electrolyte salt in the electrolytic solution, for example, the electrolytic solution is collected using any one of, or two or more of a centrifugal separation method and a solvent extraction method. Then, the electrolytic solution is analyzed using any one of, or two or more of a nuclear magnetic resonance spectroscopy (NMR) method, an atomic absorption spectroscopy (AAS) method, an ion chromatography (IC) method, and the like, thereby quantifying the content of the electrolyte salt in the electrolytic solution. In the case of using the solvent extraction method, it is preferable to use a solvent different from the solvent contained in the electrolytic solution. Further, in a case where the electrolytic solution is collected and then the electrolytic solution is handled, it is necessary to be careful that the solvent with low viscosity volatilizes.

The procedure for specifying the content (wt %) of ethylene carbonate in the solvent is, for example, as follows. In order to specify the content of ethylene carbonate in the solvent, for example, the electrolytic solution containing ethylene carbonate is collected by a procedure similar to the case of specifying the content of the electrolyte salt described above, the electrolytic solution is analyzed using any one of, or two or more of gas chromatography mass spectrometry (GC/MS), NMR, and the like to quantify each component of the solvent contained in the electrolytic solution. The content of ethylene carbonate in the solvent is specified based on the quantitative results.

The procedure for specifying the molar ratio M2/M1 is, for example, as follows. In order to specify the molar ratio M2/M1, for example, the electrolytic solution is collected by a procedure similar to the case of specifying the content of the electrolyte salt described above, and then the electrolytic solution is analyzed using any one of, or two or more of NMR, AAS, IC, and GC/MS to determine a composition ratio of all the components contained in the electrolytic solution. A molar concentration (mol/kg) of ethylene carbonate in the electrolytic solution and a molar concentration (mol/kg) of the electrolyte salt in the electrolytic solution are determined based on the composition ratio, thereby calculating the molar ratio M2/M1 (the molar concentration of ethylene carbonate/the molar concentration of electrolyte salt). In a case where the electrolytic solution is analyzed, a gas chromatography (GC) method may be further used.

[Sulfone Compound]

The sulfone compound includes any one of, or two or more of compounds represented by formulas (1), (2), and (3).

[Chem. 2]

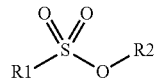

(1)

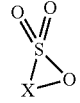

(2)

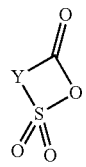

(3)

(where each of R1 and R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, provided that at least one of R1 and R2 is any one of the monovalent unsaturated hydrocarbon group and the monovalent binding group, and each of X and Y is a divalent unsaturated hydrocarbon group.)

Hereinafter, the sulfone compound represented by the formula (1) is called "first sulfone compound", the sulfone compound represented by the formula (2) is called "second sulfone compound", and the sulfone compound represented by the formula (3) is called "third sulfone compound". If necessary, the first sulfone compound, the second sulfone compound, and the third sulfone compound are collectively referred to as "sulfone compounds".

The reason why the electrolytic solution contains the sulfone compounds is that a film resulting from the sulfone compounds is formed during the electrode reaction, and thus the decomposition reaction of the electrolytic solution is suppressed by using the film. Hence, in a case where the electrolytic solution is used in the secondary battery, a film resulting from the sulfone compounds is formed on the surface of the negative electrode or the like during charge and discharge, and thus the decomposition reaction of the electrolytic solution is suppressed by using the film.

A content of the sulfone compound in the electrolytic solution is not particularly limited, but is, for example, from 0.01 wt % to 10 wt % both inclusive. This is because a sufficient amount of film is formed, and the decomposition reaction of the electrolytic solution is sufficiently suppressed.

In a case where the sulfone compound includes two or more of the first sulfone compound, the second sulfone compound, and the third sulfone compound, the "content of the sulfone compound" described above corresponds to the sum of the contents of the two or more of the sulfone compounds.

[First Sulfone Compound]

The first sulfone compound is a chain compound containing a sulfonic acid bond ($-S(=O)_2-O-$) as apparent from the formula (1).

Each of R1 and R2 is any one of a monovalent saturated hydrocarbon group, a monovalent unsaturated hydrocarbon group, and a monovalent binding group, as described above. The monovalent binding group is a group in which two or more of the monovalent saturated hydrocarbon group and the monovalent unsaturated hydrocarbon group are bound to be monovalent.

As described above, the monovalent saturated hydrocarbon group is a generic term for a monovalent group which is constituted of carbon and hydrogen and contains no unsaturated carbon bond. The unsaturated carbon bond is a carbon-carbon double bond and a carbon-carbon triple bond. The monovalent saturated hydrocarbon group may have a straight-chain structure, a branched structure with one or two or more side chains, or a cyclic structure.

Examples of the monovalent saturated hydrocarbon group include an alkyl group, a cycloalkyl group, and a monovalent saturated binding group. The monovalent saturated binding group is a group in which two or more of the alkyl group and the cycloalkyl group are bound to be monovalent.

Examples of the monovalent saturated binding group include a group in which an alkyl group and a cycloalkyl group are bound to be monovalent.

The kind of the alkyl group is not particularly limited, and examples thereof may include a methyl group, an ethyl group, a propyl group, a butyl group, a pentyl group, a hexyl group, a heptyl group, an octyl group, a nonyl group, and a decyl group.

The kind of the cycloalkyl group is not particularly limited, examples thereof may include a cyclopropyl group, a cyclobutyl group, a cyclopentyl group, a cyclohexyl group, a cycloheptyl group, a cyclooctyl group, a cyclononyl group, a cyclodecyl group, and groups other than the groups described above.

The kind of the monovalent saturated binding group is not particularly limited, and examples thereof include a group in which a methyl group and a cyclohexyl group are bound to be monovalent.

As described above, the "monovalent unsaturated hydrocarbon group" is a generic term for a monovalent group which is constituted of carbon and hydrogen and contains one or two or more unsaturated carbon bonds. The monovalent unsaturated hydrocarbon group may have a straight-chain structure, a branched structure with one or two or more side chains, or a cyclic structure.

Examples of the monovalent unsaturated hydrocarbon group include an alkenyl group, an alkynyl group, an aryl group, and a monovalent unsaturated binding group. The monovalent unsaturated binding group is a group in which two or more of the alkenyl group, the alkynyl group, and the aryl group are bound to be monovalent.

Examples of the monovalent unsaturated binding group include a group in which an alkenyl group and an alkynyl group are bound to be monovalent, a group in which an alkenyl group and an aryl group are bound to be monovalent, and a group in which an alkynyl group and an aryl group are bound to be monovalent.

The kind of the alkenyl group is not particularly limited, and examples thereof include an ethenyl group (a vinyl group), a propenyl group, a butenyl group, a pentenyl group, a hexenyl group, a heptenyl group, an octenyl group, a nonenyl group, a decenyl group, and may include groups other than the groups described above.

The kind of the alkynyl group is not particularly limited, and examples thereof include an ethynyl group, a propynyl group, a butynyl group, a pentynyl group, a hexynyl group, a heptynyl group, an octynyl group, a nonylyl group, and a decynyl group, and may include groups other than the groups described above.

The kind of the aryl group is not particularly limited, and examples thereof include a phenyl group and a naphthyl group, and may include groups other than the groups described above.

The kind of the monovalent unsaturated binding group is not particularly limited, and examples thereof include a group in which an ethenyl group and a phenyl group are bound to be monovalent and a group in which an ethynyl group and a phenyl group are bound to be monovalent.

The kind of the monovalent binding group is not particularly limited, and examples thereof include a group in which a methyl group and a phenyl group are bound to be monovalent and a group in which a cyclohexyl group and a phenyl group are bound to be monovalent.

In this regard, one or both of R1 and R2 is any one of a monovalent unsaturated hydrocarbon group and a monovalent binding group, as described above. Hence, in a case where R1 is the monovalent saturated hydrocarbon group, R2 is any one of the monovalent unsaturated hydrocarbon group and the monovalent binding group. Further, in a case where R1 is any one of the monovalent unsaturated hydrocarbon group and the monovalent binding group, R2 may be the monovalent saturated hydrocarbon group, the monovalent saturated hydrocarbon group, or the monovalent binding group.

The number of carbons of R1 is not particularly limited, and the number of carbons of R2 is not particularly limited. In particular, the sum of the number of carbons of R1 and the number of carbons of R2 is preferably from 2 to 8. This is because a film resulting from the first sulfone compound described above is easily formed while securing the solubility, compatibility, and the like of the first sulfone compound.

[Second Sulfone Compound]

The second sulfone compound is a cyclic compound containing a sulfonic acid bond (—S(=O)$_2$—O—) as apparent from the formula (2).

As described above, X is a divalent unsaturated hydrocarbon group. The "divalent unsaturated hydrocarbon group" is a generic term for a divalent group which is constituted of carbon and hydrogen and contains one or two or more unsaturated carbon bonds, as described above. The divalent unsaturated hydrocarbon group may have a straight-chain structure, a branched structure with one or more side chains, or a cyclic structure.

Examples of the divalent unsaturated hydrocarbon group include an alkenylene group, an alkynylene group, an arylene group, and a divalent unsaturated binding group. The divalent unsaturated binding group is a group in which two or more of an alkenylene group, an alkynylene group, and an arylene group are bound to be divalent.

The kind of the alkenylene group is not particularly limited, and examples thereof include an ethenylene group, a propenylene group, a butenylene group, a pentenylene group, a hexenylene group, a heptenylene group, an octenylene group, a nonenylene group, a decenylene group, and may include groups other than the groups described above.

The kind of the alkynylene group is not particularly limited. For example, the kind of the alkynyl group is not particularly limited, and examples thereof include an ethynylene group, a propynylene group, a butynylene group, a pentynylene group, a hexynylene group, a heptynylene group, an octynylene group, a nonylylene group, and a decynylene group, and may include groups other than the groups described above.

The kind of the arylene group is not particularly limited, and examples thereof include a phenylene group and a naphthylene group, and may be other groups.

The kind of the divalent unsaturated binding group is not particularly limited, and examples thereof include a group in which an ethenylene group and an ethynylene group are bound to be divalent, a group in which an ethenylene group and a phenylene group are bound to be divalent, and a group in which an ethynylene group and a phenylene group are bound to be divalent.

The number of carbons of X is not particularly limited, but is preferably from 2 to 8. This is because a film resulting from the second sulfone compound is easily formed while securing the solubility, compatibility, and the like of the second sulfone compound.

[Third Sulfone Compound]

The third sulfone compound is a cyclic compound containing a sulfonic/carboxylic anhydride bond (—C(=O)—O—S(=O)$_2$—) as apparent from the formula (3).

As described above, Y is a divalent unsaturated hydrocarbon group. The details regarding the divalent unsaturated hydrocarbon group are as described above.

The number of carbons of Y is not particularly limited, but is preferably from 2 to 10. This is because a film resulting from the third sulfone compound is easily formed while securing the solubility, compatibility, and the like of the third sulfone compound.

[Specific Examples of Sulfone Compounds]

Specific examples of the first sulfone compound include compounds represented by formulas (1-1) to (1-4). This is because a film resulting from the first sulfone compound is easily formed.

As a matter of course, the compounds represented by the formulas (1-1) to (1-4) are merely examples, and the first sulfone compound may be a compound other than the above-described compounds.

Specific examples of the second sulfone compound include compounds represented by formulas (2-1) to (2-3). This is because a film resulting from the second sulfone compound is easily formed.

As a matter of course, the compounds represented by the formulas (2-1) to (2-3) are merely examples, and the second sulfone compound may be a compound other than the above-described compounds.

Specific examples of the third sulfone compound include compounds represented by formulas (3-1) to (3-3). This is because a film resulting from the third sulfone compound is easily formed.

As a matter of course, the compounds represented by the formulas (3-1) to (3-3) are merely examples, and the third sulfone compound may be a compound other than the above-described compounds.

[Chem.3]

(1-1)

(1-2)

(1-3)

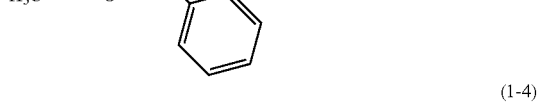
(1-4)

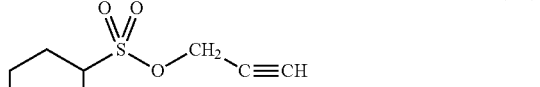
(2-1)

(2-2)

(2-3)

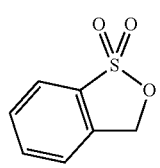

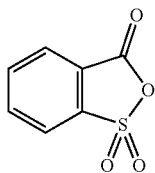
(3-1)

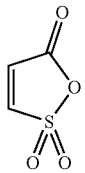
(3-2)

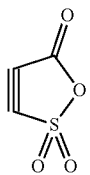
(3-3)

[Details of Solvent]

As described above, the solvent may contain any one of, or two or more of other materials together with ethylene carbonate and the sulfone compounds.

Specifically, the solvent preferably contains a high-viscosity (high dielectric constant) solvent and a low-viscosity (low dielectric constant) solvent together. This is because the dissociation and ion mobility of the electrolyte salt and the like are improved. The kind of the high-viscosity solvent may be only one kind or two kinds or more. Similarly, the kind of the low-viscosity solvent may be only one kind or two kinds or more.

The kind of the high-viscosity solvent is not particularly limited, but is, for example, a cyclic carbonate ester. Examples of the cyclic carbonate ester include propylene carbonate, in addition to the ethylene carbonate as described above.

The kind of the low-viscosity solvent is not particularly limited, but is, for example, a chain carbonate ester or a chain carboxylate ester. The low-viscosity solvent may contain only the chain carbonate ester, may contain only the chain carboxylate ester, or may contain both the chain carbonate ester and the chain carboxylate ester.

Examples of the chain carbonate ester include diethyl carbonate and ethyl methyl carbonate. Examples of the chain carboxylate ester include ethyl propionate and propyl propionate.

It is preferable that the cyclic carbonate ester contain propylene carbonate together with ethylene carbonate as described above. This is because the generation of gas resulting from the decomposition reaction of the electrolytic solution is further suppressed.

Here, a solvent may contain propylene carbonate together with ethylene carbonate, or may not necessarily contain propylene carbonate together with ethylene carbonate. In a case where the solvent contains propylene carbonate together with ethylene carbonate, a content (wt %) of propylene carbonate in the solvent is not particularly limited, but in particular, is preferably 30 wt % or less. The lower limit of the content of propylene carbonate in the solvent is not particularly limited, but is, for example, 0.01 wt %. This is because the generation of gas resulting from the decomposition reaction of the electrolytic solution is sufficiently suppressed.

The electrolytic solution may contain any one of, or two or more of other solvents together with the above-described solvent. The other solvents are, for example, any one of, or two or more of solvents such as a nonaqueous solvent (an organic solvent).

Examples of the other solvents include lactone and nitrile (mononitrile). This is because excellent battery capacity, cycle characteristics, storage characteristics, and the like are achieved.

Examples of the lactone include γ-butyrolactone and γ-valerolactone. Examples of the nitrile include acetonitrile, methoxyacetonitrile, and 3-methoxypropionitrile.

Examples of the other solvents may include 1,3-dioxolane, 4-methyl-1,3-dioxolane, 1,3-dioxane, 1,4-dioxane, N,N-dimethylformamide, N-methylpyrrolidinone, N-methyloxazolidinone, N,N'-dimethylimidazolidinone, sulfolane, trimethyl phosphate, and dimethyl sulfoxide. This is because similar advantages are obtained.

In addition, the other solvents may include an unsaturated cyclic carbonate ester, a halogenated carbonate ester, a sulfonic acid ester, an acid anhydride, a dinitrile compound, a diisocyanate compound, and the like. This is because the chemical stability of the electrolytic solution is further improved.

The unsaturated cyclic carbonate ester is a cyclic carbonate ester containing one or two or more unsaturated bonds (carbon-carbon double bonds), and examples thereof include compounds represented by formulas (4) to (6). A content of the unsaturated cyclic carbonate ester in the solvent is not particularly limited, but is, for example, from 0.01 wt % to 10 wt % both inclusive.

[Chem. 4]

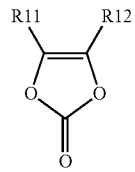
(4)

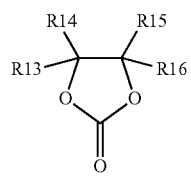
(5)

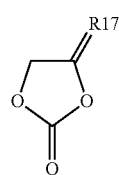
(6)

(where each of R11 and R12 is any one of a hydrogen group and an alkyl group, each of R13 to R16 is any one of a hydrogen group, an alkyl group, a vinyl group, and an allyl group, and at least one of R13 to R16 is any one of the vinyl group and the allyl group, R17 is a group represented by >CR171R172, and each of R171 and R172 is any one of a hydrogen group and an alkyl group.)

The compound represented by the formula (4) is a vinylene carbonate-type compound. R11 and R12 may be the same group as each other or may be different groups from each other. The kind of the alkyl group is not particularly limited, and examples thereof include a methyl group, an ethyl group, and a propyl group. Specific examples of the vinylene carbonate-type compound include vinylene carbonate (1,3-dioxol-2-one), methylvinylene carbonate (4-methyl-1,3-dioxol-2-one), ethylvinylene carbonate (4-ethyl-1,3-dioxol-2-one), 4,5-dimethyl-1,3-dioxol-2-one, 4,5-diethyl-1,3-dioxol-2-one, 4-fluoro-1,3-dioxol-2-one, and 4-trifluoromethyl-1,3-dioxol-2-one.

The compound represented by the formula (5) is a vinyl ethylene carbonate-type compound. R13 to R16 may be the same group as one another or may be different groups from one another. As a matter of course, some of R13 to R16 may be the same group as one another or may be different groups from one another. Specific examples of the vinyl ethylene carbonate-type compound include vinylethylene carbonate (4-vinyl-1,3-dioxolan-2-one), 4-methyl-4-vinyl-1,3-dioxolan-2-one, 4-ethyl-4-vinyl-1,3-dioxolan-2-one, 4-n-propyl-4-vinyl-1,3-dioxolan-2-one, 5-methyl-4-vinyl-1,3-dioxolan-2-one, 4,4-divinyl-1,3-dioxolan-2-one, and 4,5-divinyl-1,3-dioxolan-2-one.

The compound represented by the formula (6) is a methylene ethylene carbonate-type compound. R171 and R172 may be the same group as each other or may be different groups from each other. Specific examples of the methylene ethylene carbonate-type compound include methylene ethylene carbonate (4-methylene-1,3-dioxolan-2-one), 4,4-dimethyl-5-methylene-1,3-dioxolan-2-one, and 4,4-diethyl-5-methylene-1,3-dioxolan-2-one.

In addition, the unsaturated cyclic carbonate ester may be catechol carbonate having a benzene ring.

The halogenated carbonate ester is a cyclic or chain carbonate ester containing one or two or more halogens as constituent elements, and is a compound represented, for example, by each of formulas (7) and (8). A content of the halogenated carbonate ester in the solvent is not particularly limited, but is, for example, from 0.01 wt % to 10 wt % both inclusive.

[Chem. 5]

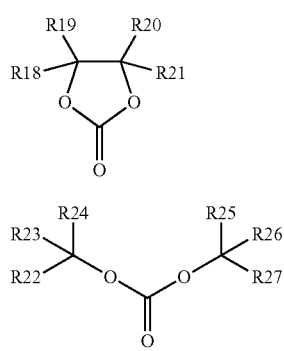

(where each of R18 to R21 is any one of a hydrogen group, a halogen group, an alkyl group, and a halogenated alkyl group, and at least one of R18 to R21 is any one of the halogen group and the halogenated alkyl group, each of R22 to R27 is any one of a hydrogen group, a halogen group, an alkyl group, and a halogenated alkyl group, and at least one of R22 to R27 is any one of the halogen group and the halogenated alkyl group.)

The compound represented by the formula (7) is a cyclic halogenated carbonate ester. R18 to R21 may be the same group as one another or may be different groups from one another. As a matter of course, some of R18 to R21 may be the same group as one another.

The kind of the halogen group is not particularly limited, but is, for example, a fluorine group, a chlorine group, a bromine group and an iodine group. In particular, the fluorine group is preferable.

Details regarding the alkyl group are as described above. The halogenated alkyl group is a group in which one or two or more hydrogen groups in an alkyl group are substituted (halogenated) by a halogen group. The details regarding the halogen group are as described above. However, the halogen group contained in the halogenated alkyl group may be only one kind or two kinds or more.

Specific examples of the cyclic halogenated carbonate ester include compounds represented by formulas (7-1) to (7-21), and also include geometric isomers thereof. In particular, 4-fluoro-1,3-dioxolan-2-one which is represented by the formula (7-1) and 4,5-difluoro-1,3-dioxolan-2-one which is represented by the formula (7-3) are preferable. A trans isomer of the 4,5-difluoro-1,3-dioxolan-2-one is more preferable than a cis isomer thereof. This is because the trans isomer is more easily available and a higher effect is achieved.

[Chem. 6]

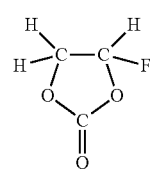

(7-1)

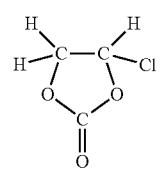

(7-2)

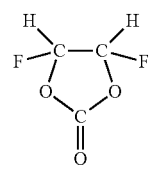

(7-3)

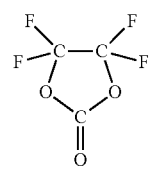

(7-4)

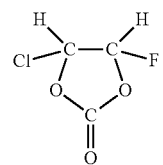

(7-5)

-continued (7-6) 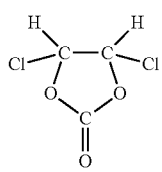

(7-7) 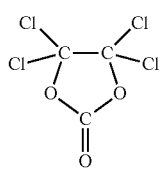

(7-8) 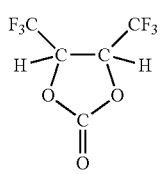

(7-9) 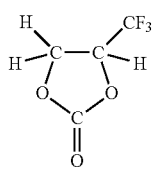

(7-10) 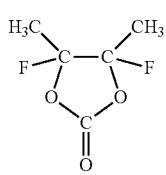

(7-11) 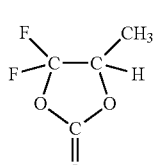

(7-12) 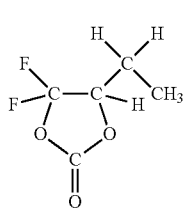

(7-13) 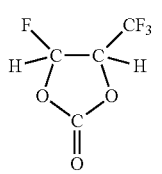

(7-14) 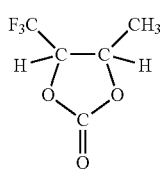

-continued (7-15) 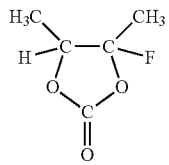

(7-16) 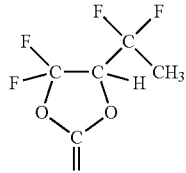

(7-17) 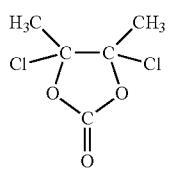

(7-18) 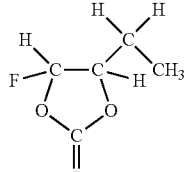

(7-19) 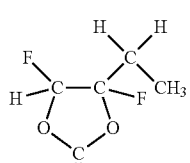

(7-20) 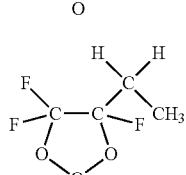

(7-21) 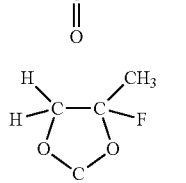

The compound represented by the formula (8) is a chain halogenated carbonate ester. R22 to R27 may be the same group as one another or may be different groups from one another. As a matter of course, some of R22 to R27 may be the same group as one another or may be different groups from one another.

Specific examples of the chain halogenated carbonate ester include fluoromethyl methyl carbonate, bis(fluoromethyl) carbonate, and difluoromethyl methyl carbonate.

Examples of the sulfonate ester include a monosulfonate ester and a disulfonate ester. A content of the sulfonate ester in the solvent is not particularly limited, but is, for example, from 0.01 wt % to 10 wt % both inclusive. However, the sulfone compounds are excluded from the term "sulfonate ester" described herein.

The monosulfonate ester may be a cyclic monosulfonate ester or a chain monosulfonate ester. Specific examples of the cyclic monosulfonate ester include sultone such as 1,3-propane sultone. Examples of the chain monosulfonate ester include a compound in which a cyclic monosulfonate ester is cleaved at a middle site.

The disulfonate ester may be a cyclic disulfonate ester or a chain disulfonate ester. Specific examples of the cyclic disulfonate ester include compounds represented by formulas (9-1) to (9-3). Specific examples of the chain disulfonate ester include a compound in which a cyclic disulfonate ester is cleaved at a middle site.

[Chem. 7]

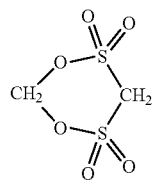

(9-1)

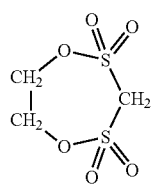

(9-2)

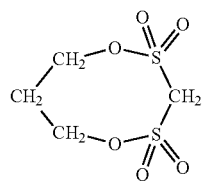

(9-3)

Examples of the acid anhydride include carboxylic anhydride, disulfonic anhydride, and carboxylic-sulfonic anhydride. A content of the acid anhydride in the solvent is not particularly limited, but is, for example, from 0.01 wt % to 10 wt % both inclusive.

Specific examples of the carboxylic anhydride include succinic anhydride, glutaric anhydride, and maleic anhydride. Specific examples of the disulfonic anhydride include ethanedisulfonic anhydride and propanedisulfonic anhydride. Specific examples of the carboxylic-sulfonic anhydride include sulfobenzoic anhydride, sulfopropionic anhydride, and sulfobutyric anhydride.

Examples of the dinitrile compound include a compound represented by NC—R81-CN (where R81 is any one of an alkylene group and an arylene group). Examples of the dinitrile compound include succinonitrile (NC—$C_2H_4$—CN), glutaronitrile (NC—$C_3H_6$—CN), adiponitrile (NC—$C_4H_8$—CN), and phthalonitrile (NC—$C_6H_4$—CN). A content of the dinitrile compound in the solvent is not particularly limited, but is, for example, from 0.5 wt % to 5 wt % both inclusive.

Examples of the diisocyanate compound include a compound represented by OCN—R82-NCO (where R82 is any one of an alkylene group and an arylene group). A content of the diisocyanate compound in the solvent is not particularly limited, but is, for example, from 0.1 wt % to 10 wt % both inclusive. Specific examples of the diisocyanate compound include OCN—$C_6H_{12}$—NCO.

[Details of Electrolyte Salt]

The electrolyte salt includes any one of, or two or more of salts such as lithium salts. However, the electrolyte salt may contain, for example, a salt other than lithium salts.

The kind of the lithium salt is not particularly limited, and examples thereof include lithium hexafluorophosphate ($LiPF_6$), lithium tetrafluoroborate ($LiBF_4$), lithium tetraphenylborate ($LiB(C_6H_5)_4$), lithium methanesulfonate ($LiCH_3SO_3$), lithium trifluoromethanesulfonate ($LiCF_3SO_3$), lithium tetrachloroaluminate ($LiAlCl_4$), dilithium hexafluorosilicate ($Li_2SiF_6$), lithium chloride (LiCl), and Lithium bromide (LiBr).

In particular, lithium hexafluorophosphate and lithium tetrafluoroborate are preferable, and lithium hexafluorophosphate is more preferable. This is because the internal resistance is reduced in the secondary battery in which the electrolytic solution is used.

The electrolytic solution may contain any one of, or two or more of other electrolyte salts together with the electrolyte salt described above.

The other electrolyte salts are, for example, compounds represented by formulas (10) to (12). R41 and R43 may be the same group as one another or may be different groups from one another. R51 to R53 may be the same group as one another or may be different groups from one another. As a matter of course, some of R51 to R53 may be the same group as one another or may be different groups from one another. R61 and R62 may be the same group as each other or may be different groups from each other.

[Chem. 8]

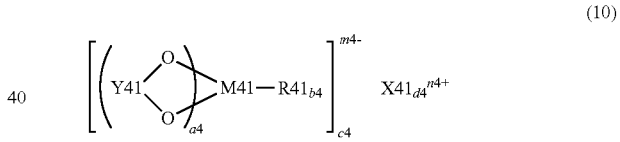

(10)

(where X41 is any one of Group 1 elements and Group 2 elements in the long form of the periodic table and aluminum (Al), M41 is any one of transition metals and Group 13 elements, Group 14 elements, and Group 15 elements in the long form of the periodic table, R41 is a halogen group, Y41 is any one of —C(=O)—R42-C(=O)—, —C(=O)—CR43$_2$- and —C(=O)—C(=O)—, where R42 is any one of an alkylene group, a halogenated alkylene group, an arylene group, and a halogenated arylene group, R43 is any one of an alkyl group, a halogenated alkyl group, an aryl group, and a halogenated aryl group, a4 is an integer of 1 to 4, b4 is an integer of 0, 2 or 4, and each of c4, d4, m4, and n4 is an integer of 1 to 3)

[Chem. 9]

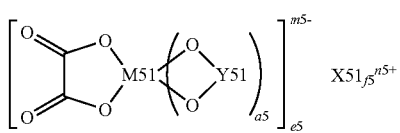

(11)

(where X51 is any one of Group 1 elements and Group 2 elements in the long form of the periodic table, M51 is any one of transition metals, and Group 13 elements, Group 14 elements, and Group 15 elements in the long form of the periodic table, Y51 is any one of —C(=O)—(CR51$_2$)$_{b5}$-C(=O)—, —R53$_2$C—(CR52$_2$)$_{c5}$-C(=O)—, —R53$_2$C—(CR52$_2$)$_{c5}$-CR53$_2$-, —R53$_2$C—(CR52$_2$)$_{c5}$-S(=O)$_2$—, —S(=O)$_2$–(CR52$_2$)$_{d5}$-S(=O)$_2$—, and —C(=O)—(CR52$_2$)$_{d5}$-S(=O)$_2$—, each of R51 and R53 is any one of a hydrogen group, an alkyl group, a halogen group, and a halogenated alkyl group, where at least one of R51's is any of the halogen group and the halogenated alkyl group, and at least one of R53's is any one of the halogen group and the halogenated alkyl group, R52 is any one of a hydrogen group, an alkyl group, a halogen group, and a halogenated alkyl group, each of a5, e5, and n5 is an integer of 1 or 2, each of b5 and d5 is an integer of 1 to 4, c5 is an integer of 0 to 4, and each of f5 and m5 is an integer of 1 to 3)

[Chem. 10]

(12)

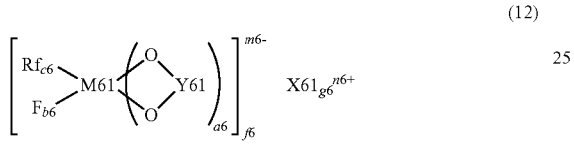

(where X61 is any one of Group 1 elements and Group 2 elements in the long form of the periodic table, M61 is any one of transition metals, and Group 13 elements, Group 14 elements, and Group 15 elements in the long form of the periodic table, Rf is any one of a fluorinated alkyl group and a fluorinated aryl group, and the number of carbons in each of the fluorinated alkyl group and the fluorinated aryl group is from 1 to 10, Y61 is any one of —C(=O)—(CR61$_2$)$_{d6}$-C(=O)—, —R62$_2$C—(CR61$_2$)$_{d6}$-C(=O)—, —R62$_2$C—(CR61$_2$)$_{d6}$-CR62$_2$-, —R62$_2$C—(CR61$_2$)$_{d6}$-S(=O)$_2$—, —S(=O)$_2$—(CR61$_2$)$_{e6}$-S(=O)$_2$—, and —C(=O)—(CR61$_2$)$_{e6}$-S(=O)$_2$—, where R61 is any one of a hydrogen group, an alkyl group, a halogen group, and a halogenated alkyl group, R62 is any one of a hydrogen group, an alkyl group, a halogen group, and a halogenated alkyl group, and at least one of R62's is any of the halogen group and the halogenated alkyl group, each of a6, f6, and n6 is an integer of 1 or 2, each of b6, c6, and e6 is an integer of 1 to 4, d6 is an integer of 0 to 4, and each of g6 and m6 is an integer of 1 to 3.)

The Group 1 elements include hydrogen (H), lithium (Li), sodium (Na), potassium (K), rubidium (Rb), cesium (Cs), and francium (Fr). The Group 2 elements include beryllium (Be), magnesium (Mg), calcium (Ca), strontium (Sr), barium (Ba), and radium (Ra). The Group 13 elements include boron (B), aluminum (Al), gallium (Ga), indium (In), and thallium (Tl). The Group 14 elements include carbon (C), silicon (Si), germanium (Ge), tin (Sn), and lead (Pb). The Group 15 elements include nitrogen (N), phosphorus (P), arsenic (As), antimony (Sb), and bismuth (Bi).

Specific examples of the compound represented by the formula (10) include compounds represented by formulas (10-1) to (10-6). Specific examples of the compound represented by the formula (11) include compounds represented by formulas (11-1) to (11-8). Specific examples of the compound represented by the formula (12) include a compound represented by formula (12-1).

[Chem. 11]

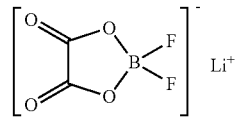 (10-1)

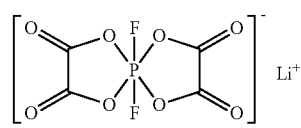 (10-2)

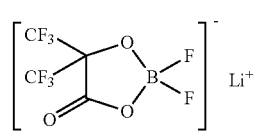 (10-3)

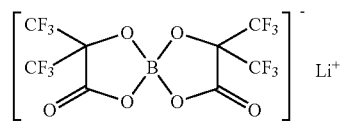 (10-4)

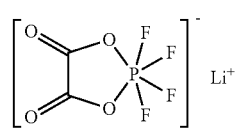 (10-5)

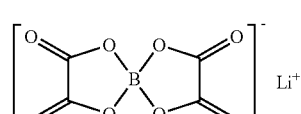 (10-6)

[Chem. 12]

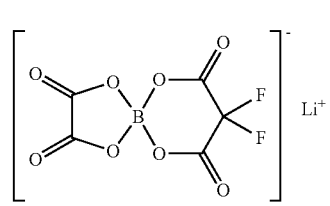 (11-1)

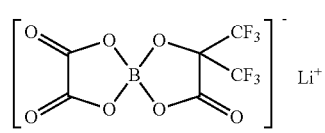 (11-2)

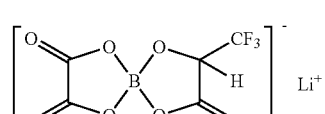 (11-3)

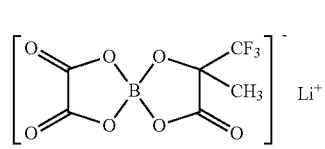 (11-4)

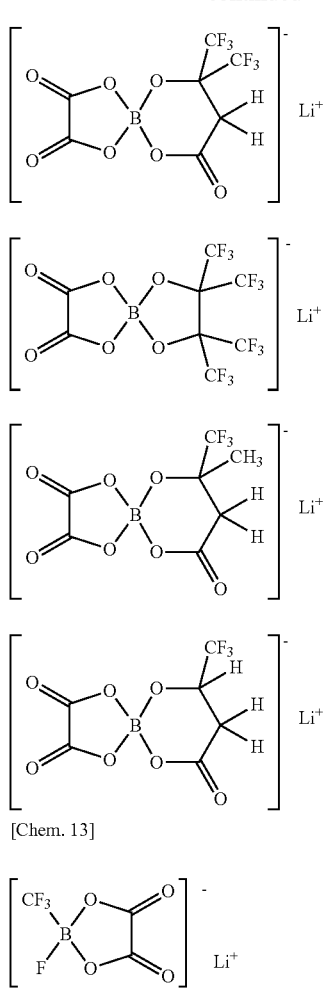

[Chem. 13]

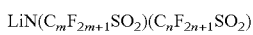

[Chem. 13]

The other electrolyte salts may be compounds represented by formulas (13) to (15). m and n may be the same value as each other, or may be different values from each other. Further, p, q, and r may be the same value as one another, or may be different values from one another. As a matter of course, some of p, q, and r may be the same value as each other.

$$\text{LiN}(C_mF_{2m+1}SO_2)(C_nF_{2n+1}SO_2) \quad (13)$$

(where each of m and n is an integer of 1 or more)

[Chem. 14]

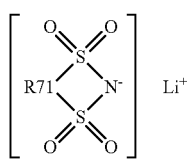 (14)

(where R71 is a straight-chain or branched perfluoroalkylene group having 2 to 4 carbons.)

$$\text{LiC}(C_pF_{2p+1}SO_2)(C_qF_{2q+1}SO_2)(C_rF_{2r+1}SO_2) \quad (15)$$

(where each of p, q, and r is an integer of 1 or more)

The compound represented by the formula (13) is a chain imide compound. Specific examples of the chain imide compound include lithium bis(fluorosulfonyl)imide (LiN(SO$_2$F)$_2$), lithium bis(trifluoromethanesulfonyl)imide (LiN(CF$_3$SO$_2$)$_2$), lithium bis(pentafluoroethanesulfonyl)imide (LiN(C$_2$F$_5$SO$_2$)$_2$), lithium (trifluoromethanesulfonyl) (pentafluoroethanesulfonyl)imide (LiN(CF$_3$SO$_2$) (C$_2$F$_5$SO$_2$)), lithium (trifluoromethanesulfonyl) (heptafluoropropanesulfonyl)imide (LiN(CF$_3$SO$_2$) (C$_3$F$_7$SO$_2$)), and lithium (trifluoromethanesulfonyl) (nonafluorobutanesulfonyl)imide (LiN(CF$_3$SO$_2$) (C$_4$F$_9$SO$_2$)).

The compound represented by the formula (14) is a cyclic imide compound. Specific examples of the cyclic imide compound include compounds represented by formulas (14-1) to (14-4).

[Chem. 15]

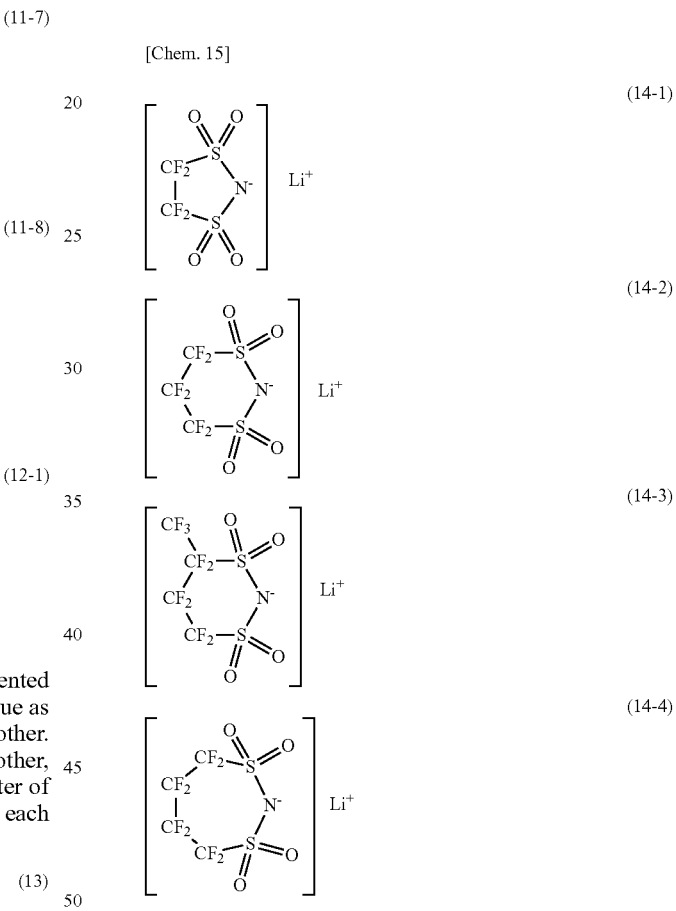

The compound represented by the formula (15) is a chain methide compound. Specific examples of the chain methide compound include lithium tris(trifluoromethanesulfonyl) methide (LiC(CF$_3$SO$_2$)$_3$).

Further, examples of other electrolyte salts may include phosphorus-fluorine-containing salts such as lithium difluorophosphate (LiPF$_2$O$_2$) and lithium fluorophosphate (Li$_2$PFO$_3$).

A content of the electrolyte salt is not particularly limited; however, in particular, the content of the electrolyte salt is preferably within a range of 0.8 mol/kg to 2.0 mol/kg both inclusive with respect to the solvent. This makes it possible to achieve high ionic conductivity. The "electrolyte salt" described herein is a sum of the content of the electrolyte salt and the content of the other electrolyte salts as described above.

[Manufacturing Method]

This electrolytic solution is manufactured, for example, by the following procedure.

In the case of manufacturing the electrolytic solution, for example, an electrolyte salt and a sulfone compound are added to a solvent containing ethylene carbonate and then the solvent is stirred to dissolve or disperse the electrolyte salt and the sulfone compound in the solvent. In this case, the mixing ratio of each of the electrolyte salt and ethylene carbonate is adjusted, whereby the three conditions described above are simultaneously satisfied with respect to the content (mol/kg) of the electrolyte salt in the electrolytic solution, the content (wt %) of ethylene carbonate in the solvent, and the molar ratio M2/M1. This results in completion of the electrolytic solution containing the electrolyte salt and the sulfone compound together with the solvent (ethylene carbonate).

[Action and Effects]

According to this electrolytic solution, the solvent (ethylene carbonate) and the sulfone compounds are contained, and the three conditions described above are simultaneously satisfied with respect to the content of the electrolyte salt in the electrolytic solution, the content of ethylene carbonate in the solvent, and the molar ratio M2/M1.

In this case, as described above, the mixing ratio of the electrolyte salt and ethylene carbonate is optimized, whereby the decomposition reaction of the electrolytic solution is suppressed while sufficiently advancing the electrode reaction using the electrolyte salt. Additionally, a film resulting from the sulfone compounds is formed during the electrode reaction, and thus the decomposition reaction of the electrolytic solution is suppressed by using the film. Thus, the generation of gas resulting from the decomposition reaction of the electrolytic solution is also suppressed.

Therefore, in the secondary battery in which the electrolytic solution is used, the discharged capacity is less likely to decrease and the secondary battery is less likely to swell, whereby it is possible to obtain excellent battery characteristics.

Particularly, when the monovalent saturated hydrocarbon group is an alkyl group or the like and the monovalent unsaturated hydrocarbon group is an alkenyl group or the like regarding the formula (1), a film resulting from the sulfone compounds is easily formed, and thus it is possible to achieve a higher effect. Further, when the divalent unsaturated hydrocarbon group is an alkenylene group or the like regarding each of the formulas (2) and (3), a film resulting from the sulfone compounds is easily formed, and thus it is possible to achieve a much higher effect.

Further, when the first sulfone compound contains the compound represented by the formula (1-1) or the like, the second sulfone compound contains the compound represented by the formula (2-1) or the like, and the third sulfone compound contains the compound represented by the formula (3-1) or the like, a film can be easily formed, and thus it is possible to achieve a higher effect.

Further, when the content of the sulfone compounds in the electrolytic solution is from 0.01 wt % to 10 wt % both inclusive, a sufficient amount of the film is formed, and thus it is possible to achieve a higher effect.

Further, when the solvent contains a cyclic carbonate ester and one or both of a chain carbonate ester and a chain carboxylate ester, the cyclic carbonate ester includes ethylene carbonate, the chain carbonate ester includes diethyl carbonate, and the chain carboxylate ester includes ethyl propionate, the generation of gas resulting from the decomposition reaction of the electrolytic solution is sufficiently suppressed, and thus it is possible to achieve a much higher effect.

Further, in a case where the solvent contains propylene carbonate and the content of propylene carbonate in the solvent is 30 wt % or less, the secondary battery is further less likely to swell, and thus it is possible to achieve a higher effect.

Further, when the electrolyte salt contains a lithium salt, ethylene carbonate can be easily solvated with a cation (a lithium ion) constituting the electrolyte salt. As a result, the secondary battery is less likely to swell, and thus it is possible to achieve a higher effect.

<2. Secondary Battery>

Subsequently, the above-described secondary battery in which the electrolytic solution is used will be described.

Figure 2:
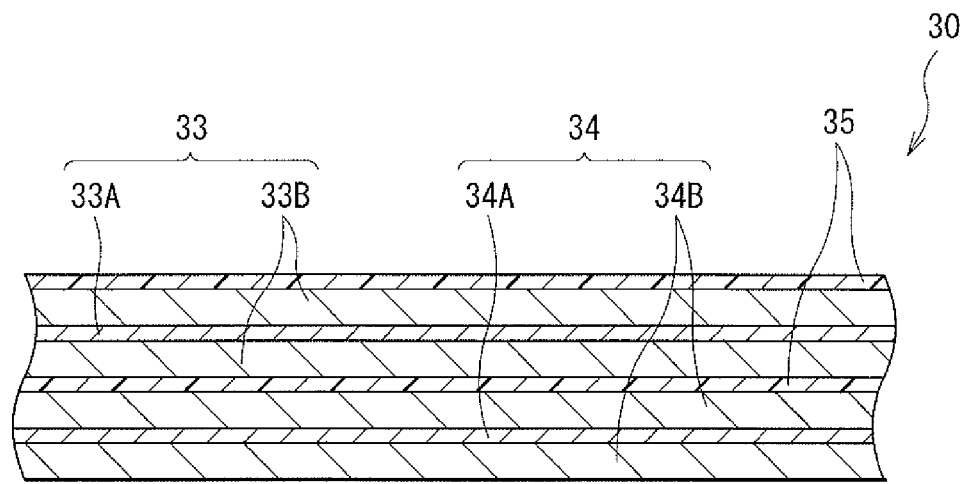
FIG. 2 is a cross-sectional view illustrating a part of the configuration of the wound electrode body illustrated in FIG. 1.

FIG. 1 illustrates a cross-sectional configuration of a secondary battery, and FIG. 2 is an enlarged cross-sectional configuration of a part of a wound electrode body 30 illustrated in FIG. 1. FIG. 1 illustrates a state in which the wound electrode body 30 and the exterior member 40 are separated from each other.

The secondary battery described herein is, for example, a lithium ion secondary battery that acquires the capacity of a negative electrode 22 through the absorption and release of lithium that is an electrode reactant.

[Overall Structure]

The secondary battery is a lithium ion secondary battery having a so-called laminated film type battery structure. For example, in the laminated film type secondary battery, the wound electrode body 30 as a battery element is housed inside the film-like exterior member 40, as illustrated in FIG. 1.

In the wound electrode body 30, for example, a positive electrode 33 and a negative electrode 34 are stacked with a separator 35 interposed therebetween, and then the positive electrode 33, the negative electrode 34, and the separator 35 are wound. The wound electrode body 30 is impregnated with an electrolytic solution that is a liquid electrolyte. In other words, the wound electrode body 30 housed inside the film-like exterior member 40 includes the positive electrode 33, the negative electrode 34, and the electrolytic solution.

A positive electrode lead 31 is attached to the positive electrode 33, and a negative electrode lead 32 is attached to the negative electrode 34. The outermost peripheral part of the wound electrode body 30 is protected by a protective tape.

Each of the positive electrode lead 31 and the negative electrode lead 32 is led out from the inside to the outside of the exterior member 40 in a same direction, for example. The positive electrode lead 31 includes any one of, or two or more of conductive materials such as aluminum (Al). The negative electrode lead 32 includes any one of, or two or more of conductive materials such as copper (Cu), nickel (Ni), and stainless steel. These conductive materials have, for example, a thin-plate shape or a mesh shape.

The exterior member 40 is, for example, one film that is foldable in a direction of an arrow R illustrated in FIG. 1, and the exterior member 40 has a depression for containing the wound electrode body 30 in part thereof. The exterior member 40 is, for example, a laminated film in which a fusion layer, a metal layer, and a surface protective layer are laminated in this order. In a process of manufacturing the secondary battery, the exterior member 40 is folded so that the fusion layers are opposed to each other with the wound electrode body 30 interposed therebetween, and thereafter outer periphery edges of the fusion layers are fusion-bonded to each other. However, two laminated films bonded to each other using an adhesive may form the exterior member 40. The fusion layer is, for example, a film made of any one of, or two or more of polyethylene and polypropylene. The metal layer includes, for example, any one of, or two or more of an aluminum foil and the like. The surface protective layer is, for example, a film made of any one of, or two or more of nylon, polyethylene terephthalate, and the like.

In particular, the exterior member 40 is preferably an aluminum laminated film in which a polyethylene film, an aluminum foil, and a nylon film are laminated in this order. However, the exterior member 40 may be a laminated film having any other laminated structure, a polymer film such as polypropylene, or a metal film.

For example, an adhesive film 41 for prevention of outside air intrusion is inserted between the exterior member 40 and the positive electrode lead 31. In addition, for example, the adhesive film 41 mentioned above is inserted between the exterior member 40 and the negative electrode lead 32. The adhesive film 41 contains a material having adhesibility with respect to both the positive electrode lead 31 and the negative electrode lead 32. Examples of the material having adhesibility include a polyolefin resin, and more specific examples thereof include any one of, or two or more of polyethylene, polypropylene, modified polyethylene, and modified polypropylene.

[Positive Electrode]

For example, as illustrated in FIG. 2, the positive electrode 33 includes a positive electrode current collector 33A and a positive electrode active material layer 33B provided on both sides of the positive electrode current collector 33A. However, the positive electrode active material layer 33B may be provided only on one side of the positive electrode current collector 33A.

The positive electrode current collector 33A includes, for example, any one of, or two or more of conductive materials. The kind of the conductive material is not particularly limited, but is, for example, a metal material such as aluminum, nickel or stainless steel. The positive electrode current collector 33A may be a single layer or a multiple layer.

The positive electrode active material layer 33B includes, as a positive electrode active material, any one of, or two or more of positive electrode materials capable of absorbing and releasing lithium. However, the positive electrode active material layer 33B may further include any one of, or two or more of other materials such as a positive electrode binder and a positive electrode conductive agent, in addition to the positive electrode active material.

The positive electrode material is preferably a lithium-containing compound, and more specifically, it is preferably one or both of a lithium-containing composite oxide and a lithium-containing phosphate compound. This makes it possible to achieve high energy density.

The lithium-containing composite oxide is an oxide containing lithium and one or two or more other elements (elements other than lithium) as constituent elements, and has, for example, a layered rock salt-type crystal structure or a spinel-type crystal structure. The lithium-containing phosphate compound is a phosphate compound containing lithium and one or two or more other elements as constituent elements, and has, for example, an olivine-type crystal structure.

The kinds of the other elements are not particularly limited as long as the elements correspond to any one of, or two or more of arbitrary elements. In particular, the other elements preferably correspond to any one of, or two or more of the elements that belong to Groups 2 to 15 in the long form of the periodic table. More specifically, the other elements more preferably include any one of, or two or more of metal elements of nickel (Ni), cobalt (Co), manganese (Mn), and iron (Fe). This makes it possible to obtain a high voltage.

Examples of the lithium-containing composite oxide having the layered rock salt-type crystal structure include compounds represented by formulas (21) to (23).

$$Li_aMn_{(1-b-c)}Ni_bM11_cO_{(2-d)}F_e \quad (21)$$

(where M11 is at least one of cobalt (Co), magnesium (Mg), aluminum (Al), boron (B), titanium (Ti), vanadium (V), chromium (Cr), iron (Fe), copper (Cu), zinc (Zn), zirconium (Zr), molybdenum (Mo), tin (Sn), calcium (Ca), strontium (Sr), and tungsten (W), a to e satisfy $0.8 \leq a \leq 1.2$, $0 < b < 0.5$, $0 \leq c \leq 0.5$, $(b+c) < 1$, $-0.1 \leq d \leq 0.2$, and $0 \leq e \leq 0.1$, where the composition of lithium varies depending on charge and discharge states, and a is a value in a completely discharged state.)

$$Li_aNi_{(1-b)}M12_bO_{(2-c)}F_d \quad (22)$$

(where M12 is at least one of cobalt (Co), manganese (Mn), magnesium (Mg), aluminum (Al), boron (B), titanium (Ti), vanadium (V), chromium (Cr), iron (Fe), copper (Cu), zinc (Zn), molybdenum (Mo), tin (Sn), calcium (Ca), strontium (Sr), and tungsten (W), a to d satisfy $0.8 \leq a \leq 1.2$, $0.005 \leq b \leq 0.5$, $-0.1 \leq c \leq 0.2$, and $0 \leq d \leq 0.1$, where the composition of lithium varies depending on charge and discharge states, and a is a value in a completely discharged state.)

$$Li_aCO_{(1-b)}M13_bO_{(2-c)}F_d \quad (23)$$

(where M13 is at least one of nickel (Ni), manganese (Mn), magnesium (Mg), aluminum (Al), boron (B), titanium (Ti), vanadium (V), chromium (Cr), iron (Fe), copper (Cu), zinc (Zn), molybdenum (Mo), tin (Sn), calcium (Ca), strontium (Sr), and tungsten (W), a to d satisfy $0.8 \leq a \leq 1.2$, $0 \leq b < 0.5$, $-0.1 \leq c \leq 0.2$, and $0 \leq d \leq 0.1$, where the composition of lithium varies depending on charge and discharge states, and a is a value in a completely discharged state.)

Examples of the lithium-containing composite oxide having the layered rock salt-type crystal structure may include a compound represented by formula (24). This compound is a lithium nickel-containing composite oxide that contains nickel as a constituent element and has a relatively high content ratio of nickel.

$$Li_xCo_yNi_zM_{1-y-z}O_{b-a}X_e \quad (24)$$

(where M is at least one of boron (B), magnesium (Mg), aluminum (Al), titanium (Ti), chromium (Cr), manganese (Mn), gallium (Ga), yttrium (Y), zirconium (Zr), molybdenum (Mo), strontium (Sr), cesium (Cs), barium (Ba), indium (In), and antimony (Sb), X is a halogen element, x, y, z, a, and b satisfy $0.8 < x \leq 1.2$, $0 \leq y \leq 1.0$, $0.5 \leq z \leq 1.0$, $0 \leq a \leq 1.0$, $1.8 \leq b \leq 2.2$, and $y < z$.

Specific examples of the lithium-containing composite oxide having the layered rock salt-type crystal structure include $LiNiO_2$, $LiCoO_2$, $LiCo_{0.98}Al_{0.01}Mg_{0.01}O_2$, $LiNi_{0.5}Co_{0.2}Mn_{0.3}O_2$, $LiNi_{0.8}Co_{0.15}Al_{0.05}O_2$, $LiNi_{0.33}Co_{0.33}Mn_{0.33}O_2$, $Li_{1.2}Mn_{0.52}Co_{0.175}Ni_{0.1}O_2$, and $Li_{1.15}(Mn_{0.65}Ni_{0.22}Co_{0.13})O_2$.

In a case where the lithium-containing composite oxide having the layered rock salt-type crystal structure includes nickel, cobalt, manganese, and aluminum as constituent elements, the atomic ratio of the nickel is preferably 50 atomic % or more. This makes it possible to achieve high energy density.

Examples of the lithium-containing composite oxide having the spinel-type crystal structure include a compound represented by formula (25).

$$Li_aMn_{(2-b)}M14_bO_cF_d \quad (25)$$

(where M14 is at least one of cobalt (Co), Nickel (Ni), magnesium (Mg), aluminum (Al), boron (B), titanium (Ti), vanadium (V), chromium (Cr), iron (Fe), copper (Cu), zinc (Zn), molybdenum (Mo), tin (Sn), calcium (Ca), strontium (Sr), and tungsten (W), a to d satisfy $0.9 \le a \le 1.1$, $0 \le b \le 0.6$, $3.7 \le c \le 4.1$, and $0 \le d \le 0.1$, where the composition of lithium varies depending on charge and discharge states, and a is a value in a completely discharged state.)

Specific examples of the lithium-containing composite oxide having the spinel-type crystal structure include $LiMn_2O_4$.

Examples of the lithium-containing phosphate compound having the olivine-type crystal structure include a compound represented by formula (26).

$$Li_aM15PO_4 \quad (26)$$

(where M15 is at least one of cobalt (Co), manganese (Mn), iron (Fe), nickel (Ni), magnesium (Mg), aluminum (Al), boron (B), titanium (Ti), vanadium (V), niobium (Nb), copper (Cu), zinc (Zn), molybdenum (Mo), calcium (Ca), strontium (Sr), tungsten (W), and zirconium (Zr), a satisfies $0.9 \le a \le 1.1$, where the composition of lithium varies depending on charge and discharge states, and a is a value in a completely discharged state.)

Specific examples of the lithium-containing phosphate compound having the olivine-type crystal structure include $LiFePO_4$, $LiMnPO_4$, $LiFe_{0.5}Mn_{0.5}PO_4$, and $LiFe_{0.3}Mn_{0.7}PO_4$.

The lithium-containing composite oxide may be, for example, a compound represented by formula (27).

$$(Li_2MnO_3)_x(LiMnO_2)_{1-x} \quad (27)$$

(where x satisfies $0 \le x \le 1$, it is to be noted that the composition of lithium varies depending on charge and discharge states, and x is a value in a completely discharged state.)

In addition, the positive electrode material may be, for example, any one of, or two or more of an oxide, a disulfide, a chalcogenide, and a conductive polymer. Examples of the oxide include titanium oxide, vanadium oxide, and manganese dioxide. Examples of the disulfide include titanium disulfide and molybdenum sulfide. Examples of the chalcogenide include niobium selenide. Examples of the conductive polymer include sulfur, polyaniline, and polythiophene. The positive electrode material may be any material other than the materials described above.

The positive electrode binder includes any one of, or two or more of, for example, synthetic rubbers and polymer compounds. Examples of the synthetic rubbers include a styrene-butadiene-based rubber, a fluorine-based rubber, and ethylene propylene diene. Examples of the polymer compounds include polyvinylidene fluoride, and polyimide.

The positive electrode conductive agent includes any one of, or two or more of, for example, carbon materials. Examples of the carbon materials include graphite, carbon black, acetylene black, and ketjen black. Alternatively, the positive electrode conductive agent may be a metal material, a conductive polymer, or the like as long as the positive electrode conductive agent is a material having conductivity.

[Negative Electrode]

As illustrated in FIG. 2, the negative electrode 34 includes, for example, a negative electrode current collector 34A and a negative electrode active material layer 34B provided on both sides of the negative electrode current collector 34A. Alternatively, the negative electrode active material layer 34B may be provided only on one side of the negative electrode current collector 34A.

The negative electrode current collector 34A includes, for example, any one of, or two or more of conductive materials. The kind of the conductive material is not particularly limited, but is, for example, a metal material such as copper, aluminum, nickel or stainless steel. The negative electrode current collector 34A may be a single layer or a multiple layer.

A surface of the negative electrode current collector 34A is preferably roughened. This makes it possible to improve adhesibility of the negative electrode active material layer 34B with respect to the negative electrode current collector 34A by a so-called anchor effect. In this case, it may be only necessary to roughen the surface of the negative electrode current collector 34A at least in a region opposed to the negative electrode active material layer 34B. Examples of a roughening method include a method of forming fine particles with the use of electrolytic treatment. Through the electrolytic treatment, fine particles are formed on the surface of the negative electrode current collector 34A in an electrolytic bath by an electrolytic method, as a result of which irregularities are generated on the surface of the negative electrode current collector 34A. A copper foil fabricated by the electrolytic method is generally referred to as "electrolytic copper foil".

The negative electrode active material layer 34B includes, as a negative electrode active material, any one of, or two or more of negative electrode materials capable of absorbing and releasing lithium. However, the negative electrode active material layer 34B may further include any one of, or two or more of other materials such as a negative electrode binder and a negative electrode conductive agent, in addition to the negative electrode active material.

The chargeable capacity of the negative electrode material is preferably higher than the discharged capacity of the positive electrode 33 in order to prevent lithium metal from being unintentionally deposited on the negative electrode 34 in the process of charging. In other words, the electrochemical equivalent of the negative electrode material capable of absorbing and releasing lithium is preferably larger than the electrochemical equivalent of the positive electrode 33.

The negative electrode material is, for example, any one of, or two or more of carbon materials. This is because a change in the crystal structure during absorbing and releasing of lithium is extremely small so that high energy density is stably achieved. Further, this is because the carbon material also functions as the negative electrode conductive agent, thus improving the conductivity of the negative electrode active material layer 34B.

Examples of the carbon material include graphitizable carbon, non-graphitizable carbon, and graphite. However, an interplanar spacing of (002) plane in the non-graphitizable carbon is preferably 0.37 nm or more, and an interplanar spacing of (002) plane in the graphite is preferably 0.34 nm or less. More specific examples of the carbon material include pyrolytic carbons, cokes, glassy carbon fibers, an organic polymer compound fired body, activated carbon, and carbon black. Examples of the cokes include pitch coke, needle coke, and petroleum coke. The organic polymer compound fired body is a substance in which a polymer compound such as a phenol resin or a furan resin is fired (carbonized) at an appropriate temperature. In addition, the carbon material may be low-crystalline carbon that is subjected to heat treatment at a temperature of about 1000° C.

or lower, or may be amorphous carbon. A shape of the carbon material may be any of fibrous, spherical, granular, and scaly.

Further, the negative electrode material is, for example, a material (a metal-based material) that contains any one of, or two or more of metal elements and metalloid elements as constituent elements. This makes it possible to achieve high energy density.

The metal-based material may be any one of a simple substance, an alloy, and a compound, may be two or more thereof, or may be a material having one or two or more phases thereof at least in part. However, the alloy includes a material containing one or more metal elements and one or more metalloid elements, in addition to a material that is made of two or more metal elements. Further, the alloy may include a non-metal element. Examples of a structure of the metal-based material include a solid solution, a eutectic crystal (a eutectic mixture), an intermetallic compound, and a structure in which two or more thereof coexist.

The metal elements and metalloid elements may be, for example, any one of, or two or more of metal elements and metalloid elements capable of forming an alloy with lithium. Specific examples of the metal elements and metalloid elements include magnesium (Mg), boron (B), aluminum (Al), gallium (Ga), indium (In), silicon (Si), germanium (Ge), tin (Sn), lead (Pb), bismuth (Bi), cadmium (Cd), silver (Ag), zinc, hafnium (Hf), zirconium, yttrium (Y), palladium (Pd), and platinum (Pt).

In particular, one or both of silicon and tin is preferable. This is because the ability to absorb and release lithium is excellent, thus achieving a remarkably high energy density.

A material that contains one or both of silicon and tin as a constituent element may be any one of a simple substance, an alloy, and a compound of silicon, may be any one of a simple substance, an alloy, and a compound of tin, may be two or more thereof, or may be a material that has one or two or more phases thereof at least in part. The term "simple substance" explained herein consistently means a simple substance (which may contain trace amounts of impurities) in a general sense, and thus the term does not necessarily mean a purity of 100%.

The alloy of silicon contains, for example, any one of, or two or more of tin, nickel, copper, iron, cobalt, manganese, zinc, indium, silver, titanium, germanium, bismuth, antimony, and chromium, as constituent elements other than silicon. The compound of silicon contains, for example, any one of, or two or more of carbon and oxygen, as constituent elements other than silicon. The compound of silicon may contain, for example, any one of, or two or more of the series of elements described related to the alloy of silicon, as constituent elements other than silicon.

Specific examples of the alloy of silicon and the compound of silicon include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, $SiC$, $Si_3N_4$, $Si_2N_2O$, $SiO_v$ ($0<v\leq2$), and LiSiO. In this regard, v in $SiO_v$ may be $0.2<v<1.4$.

The alloy of tin contains, for example, any one of, or two or more of silicon, nickel, copper, iron, cobalt, manganese, zinc, indium, silver, titanium, germanium, bismuth, antimony, and chromium, as a constituent element other than tin. The compound of tin contains, for example, any one of, or two or more of carbon and oxygen, as constituent elements other than tin. It is to be noted that the compound of tin may contain, for example, any one of, or two or more of the series of elements described related to the alloy of tin, as constituent elements other than tin.

Specific examples of the alloy of tin and the compound of tin include $SnO_w$ ($0<w\leq2$), $SnSiO_3$, LiSnO, and $Mg_2Sn$.

Particularly, the material that contains tin as a constituent element is preferably, for example, a material (Sn-containing material) that contains, together with tin as a first constituent element, a second constituent element and a third constituent element. The second constituent element includes, for example, any one of, or two or more of cobalt, iron, magnesium, titanium, vanadium, chromium, manganese, nickel, copper, zinc, gallium, zirconium, niobium, molybdenum, silver, indium, cesium (Ce), hafnium (Hf), tantalum, tungsten, bismuth, and silicon. The third constituent element includes, for example, any one of, or two or more of boron, carbon, aluminum, and phosphorus. This is because the Sn-containing material contains the second constituent element and the third constituent element, thereby achieving a high battery capacity, excellent cycle characteristics, and the like.

In particular, the Sn-containing material is preferably a material (SnCoC-containing material) that contains tin, cobalt, and carbon as constituent elements. In the SnCoC-containing material, for example, a content of carbon is from 9.9 mass % to 29.7 mass % both inclusive, and a ratio of contents of tin and cobalt (Co/(Sn+Co)) is from 20 mass % to 70 mass % both inclusive. This makes it possible to achieve high energy density.

The SnCoC-containing material has a phase that contains tin, cobalt, and carbon, and the phase is preferably low-crystalline or amorphous. This phase is a reaction phase capable of reacting with lithium, and thus excellent characteristics are achieved due to the presence of the reaction phase. A half-value width (a diffraction angle 2θ) of a diffraction peak obtained by X-ray diffraction of this reaction phase is preferably 1° or more in a case where a CuKα ray is used as a specific X-ray and a sweep rate is 1°/min. This is because lithium is absorbed and released more smoothly, and reactivity with the electrolytic solution is reduced. In some cases, the SnCoC-containing material includes a phase that contains simple substances of the respective constituent elements or part thereof, in addition to the low-crystalline or amorphous phase.

Whether the diffraction peak obtained by X-ray diffraction corresponds to the reaction phase capable of reacting with lithium can be easily determined by comparing X-ray diffraction charts before and after an electrochemical reaction with lithium. For example, when the position of the diffraction peak is changed between before and after the electrochemical reaction with lithium, the peak corresponds to the reaction phase capable of reacting with lithium. In this case, for example, the diffraction peak of the low-crystalline or amorphous reaction phase is observed at 2θ=20° to 50°. Such a reaction phase includes, for example, the respective constituent elements described above, and it is considered that the phase is low crystallized or amorphized mainly due to the presence of carbon.

In the SnCoC-containing material, at least part of the carbon as a constituent element is preferably bonded to a metal element or a metalloid element, both of which are other constituent elements. This is because aggregation or crystallization of tin and the like is suppressed. It is possible to confirm the bonding state of the elements, for example, by X-ray photoelectron spectroscopy (XPS). In a commercially available device, for example, an Al-Kα ray or a Mg-Kα ray is used as a soft X-ray. In a case where at least part of carbon is bonded to a metal element, a metalloid element, or the like, a peak of a synthetic wave of is orbit of carbon (C1s) appears in a region lower than 284.5 eV. Energy calibration is made so that a peak of 4f orbit of a gold atom (Au4f) is obtained at 84.0 eV. In this case, generally, surface contaminated carbon is present on the surface of the substance. Hence, a peak of Cis of the surface contaminated carbon is set to 284.8 eV, and the peak is used as energy reference. In the XPS measurement, a waveform of the peak of Cis of the surface contaminated carbon is obtained in a form that includes the peak of the surface contaminated carbon and the peak of the carbon in the SnCoC-containing material. Therefore, both the peaks are separated, for example, by analysis with the use of commercially available software. In the analysis of the waveform, a position of the main peak that exists on the lowest binding energy side is regarded as the energy reference (284.8 eV).

This SnCoC-containing material is not limited to a material (SnCoC) that contains only tin, cobalt, and carbon as constituent elements. The SnCoC-containing material may further contain any one of, or two or more of, for example, silicon, iron, nickel, chromium, indium, niobium, germanium, titanium, molybdenum, aluminum, phosphorus, gallium, and bismuth, as constituent elements, in addition to tin, cobalt, and carbon.

In addition to the SnCoC-containing material, a material (a SnCoFeC-containing material) that contains tin, cobalt, iron, and carbon as constituent elements is also preferable. This SnCoFeC-containing material has an arbitrary composition. To give an example, in a case where a content of iron is set to be smaller, a content of carbon is from 9.9 mass % to 29.7 mass % both inclusive, the content of iron is from 0.3 mass % to 5.9 mass % both inclusive, and a ratio of contents of tin and cobalt (Co/(Sn+Co)) is from 30 mass % to 70 mass % both inclusive. Alternatively, in a case where the content of iron is set to be larger, the content of carbon is from 11.9 mass % to 29.7 mass % both inclusive, the ratio of contents of tin, cobalt, and iron ((Co+Fe)/(Sn+Co+Fe)) is from 26.4 mass % to 48.5 mass % both inclusive, and the ratio of contents of cobalt and iron (Co/(Co+Fe)) is from 9.9 mass % to 79.5 mass % both inclusive. This is because high energy density is achieved in such composition ranges. Physical properties (such as a half-value width) of the SnCoFeC-containing material are similar to physical properties of the SnCoC-containing material as described above.

In addition, the negative electrode material may be any one of, or two or more of, for example, a metal oxide and a polymer compound. Examples of the metal oxide include iron oxide, ruthenium oxide, and molybdenum oxide. Examples of the polymer compound include polyacetylene, polyaniline, and polypyrrole.

In particular, the negative electrode material preferably contains both the carbon material and the metal-based material for the following reason.

The metal-based material, particularly, a material containing one or both of silicon and tin as constituent elements has an advantage of high theoretical capacity. In contrast, the material has a concern about being likely to expand and shrink violently during charging and discharging. Meanwhile, the carbon material has a concern about being low in theoretical capacity, but at the same time, has an advantage of being unlikely to expand and shrink during charging and discharging. Therefore, the use of both the carbon material and the metal-based material suppresses the expansion and shrinkage during charging and discharging while achieving high theoretical capacity (in other words, battery capacity).

The negative electrode active material layer 34B is formed by any one, or two or more of methods such as a coating method, a vapor phase method, a liquid phase method, a thermal spraying method, and a firing method (sintering method). The coating method is, for example, a method of mixing a negative electrode active material in the particle (powder) form with a negative electrode binder or the like, dispersing the mixture in an organic solvent or the like, and then applying the resulting mixture to the negative electrode current collector 34A. Examples of the vapor phase method include a physical deposition method and chemical deposition method. More specifically, examples of the vapor phase method include a vacuum deposition method, a sputtering method, an ion plating method, a laser ablation method, a thermal chemical vapor deposition method, a chemical vapor deposition (CVD) method, and a plasma chemical vapor deposition method. Examples of the liquid phase method include an electrolytic plating method and an electroless plating method. The thermal spraying method is a method of spraying a molten or a semi-molten negative electrode active material onto the surface of the negative electrode current collector 34A. The firing method is, for example, a method of applying a mixture dispersed in an organic solvent or the like to the negative electrode current collector 34A by using the coating method, and then performing a heat treatment at a temperature higher than the melting point of the negative electrode binder or the like. For example, it is possible to use an atmospheric firing method, a reactive firing method, a hot press firing method or the like as the firing method.

In this secondary battery, the electrochemical equivalent of the negative electrode material capable of absorbing and releasing lithium is larger than the electrochemical equivalent of the positive electrode in order to prevent lithium from being unintentionally deposited on the negative electrode 34 in the process of charging as described above. Further, in a case where an open circuit voltage (i.e., a battery voltage) in a completely charged state is 4.25 V or more, the release amount of the lithium per unit mass is increased even with the use of the same positive electrode active material as compared with a case where the open circuit voltage in the completely charged state is 4.20 V, and thus the amount of the positive electrode active material and the amount of the negative electrode active material are adjusted depending on the release amount. As a result, high energy density is achieved.

The open circuit voltage in the completely charged state (charge termination voltage) is not particularly limited, and it is preferably 4.2 V or more, as described above. Particularly, the open circuit voltage in the completely charged state is preferably 4.25 V or more, and more preferably 4.35 V or more. This is because even if the open circuit voltage in the completely charged state is extremely high, it is possible to obtain advantages based on the optimization of the mixing ratio of the electrolyte salt and ethylene carbonate described above, and thus it is possible to obtain excellent battery characteristics. The discharge termination voltage is not particularly limited, but is, for example, 3.0 V or less.

[Separator]

For example, the separator 35 is disposed between the positive electrode 33 and the negative electrode 34, as illustrated in FIG. 2. The separator 35 separates the positive electrode 33 and the negative electrode 34, and allows passage of lithium ions while preventing a short circuit due to the current caused by the contact between both the positive electrode 33 and the negative electrode 34.

The separator 35 is, for example, any one of, or two or more of porous films such as a synthetic resin and ceramics, and may be a laminated film in which two or more porous films are laminated. Examples of the synthetic resin include polytetrafluoroethylene, polypropylene, and polyethylene.

Particularly, the separator 35 may include, for example, the above-described porous film (a base material layer), and a polymer compound layer provided on one side or both sides of the base material layer. This is because the adhesibility of the separator 35 with respect to each of the positive electrode 33 and the negative electrode 34 is improved, thereby suppressing the warping of the wound electrode body 30. Thus, the inhibited decomposition reaction of the electrolytic solution, and also, the suppressed leakage of the electrolytic solution with which the base material layer is impregnated, make the electric resistance less likely to increase even with repeated charging and discharging, and suppress the swelling of the battery.

The polymer compound layer includes, for example, a polymer compound such as polyvinylidene fluoride. This is because the polymer material has excellent physical strength, and is electrochemically stable. However, the polymer compound may be a compound other than polyvinylidene fluoride. In the case of forming the polymer compound layer, for example, the base material layer is coated with a solution produced by dissolving a polymer compound in an organic solvent or the like, and then the base material layer is dried. The base material layer is immersed in the solution, and thereafter the base material layer may be dried. This polymer compound layer may include any one of, or two or more of insulating particles such as inorganic particles. The kind of inorganic particles is, for example, aluminum oxide or aluminum nitride.

[Electrolytic Solution]

The electrolytic solution has a configuration similar to that of the electrolytic solution of the present technology described above. That is, in the electrolytic solution, the solvent contains ethylene carbonate, and the mixing ratio of the electrolyte salt and ethylene carbonate is optimized. Hence, the three conditions described above are simultaneously satisfied with respect to the content of the electrolyte salt in the electrolytic solution, the content of ethylene carbonate in the solvent, and the molar ratio M2/M1.

An electrolyte layer as a gel electrolyte may be used in place of the electrolytic solution as a liquid electrolyte. The electrolyte layer is formed, for example, on a surface of one or both of the positive electrode 33 and the negative electrode 34. Further, the electrolyte layer contains an electrolytic solution and a polymer compound that holds the electrolytic solution. The configuration of the electrolytic solution is as described above.

The polymer compound contains, for example, any one of, or two or more of polyacrylonitrile, polyvinylidene fluoride, polytetrafluoroethylene, polyhexafluoropropylene, polyethylene oxide, and polypropylene oxide. In addition, the polymer compound may be a copolymer. The copolymer is, for example, a copolymer of vinylidene fluoride and hexafluoropyrene.

[Operation]

This secondary battery operates, for example, as follows.

When the secondary battery is charged, lithium ions are released from the positive electrode 33, and the lithium ions are absorbed in the negative electrode 34 through the electrolyte layer 36. Meanwhile, when the secondary battery is discharged, lithium ions are released from the negative electrode 34, and the lithium ions are absorbed in the positive electrode 33 through the electrolyte layer 36.

[Manufacturing Method]

This secondary battery is manufactured, for example, by the following procedure.

In the case of fabricating the positive electrode 33, first, a positive electrode active material is mixed with a positive electrode binder, a positive electrode conductive agent or the like, if necessary, thereby preparing a positive electrode mixture. Then, the positive electrode mixture is dispersed in an organic solvent or the like, thereby preparing a paste-like positive electrode mixture slurry. Thereafter, the positive electrode mixture slurry is applied to both sides of the positive electrode current collector 33A, and the positive electrode mixture slurry is dried, thereby forming the positive electrode active material layer 33B. After that, the positive electrode active material layer 33B is subjected to compression-molding with the use of a roll press machine or the like, while heating the positive electrode active material layer 33B, if necessary. In this case, compression-molding may be repeated a plurality of times.

In the case of fabricating the negative electrode 34, the negative electrode active material layer 34B is formed on both sides of the negative electrode current collector 34A by a fabrication procedure similar to that of the positive electrode 33. Specifically, a negative electrode mixture is prepared by mixing a negative electrode active material with a negative positive electrode binder, a negative electrode conductive agent or the like, and then the negative electrode mixture is dispersed in an organic solvent or the like to prepare a paste-like negative electrode mixture slurry. Then, the negative electrode mixture slurry is applied to both sides of the negative electrode current collector 34A, and the negative electrode mixture slurry is dried, thereby forming the negative electrode active material layer 34B. Finally, the negative electrode active material layer 34B is subjected to compression-molding with the use of a roll press machine.

In the case of assembling the secondary battery, the positive electrode lead 31 is attached to the positive electrode current collector 33A by using a welding method or the like, and the negative electrode lead 32 is attached to the negative electrode current collector 34A by using a welding method or the like. Then, the positive electrode 33 and the negative electrode 34 are stacked with the separator 35 interposed therebetween, and thereafter the positive electrode 33, the negative electrode 34, and the separator 35 are wound to form a wound body as a precursor of the wound electrode body 30. After that, the protective tape is attached to the outermost peripheral part of the wound body. Thereafter, the exterior member 40 is folded so as to sandwich the wound body therebetween, and remaining outer periphery edges of the exterior member 40 excluding one outer periphery edge thereof are then bonded by the use of a thermal fusion bonding method or the like, thereby housing the wound body inside the pouch-shaped exterior member 40. Finally, the electrolytic solution is injected into the pouch-shaped exterior member 40, and then the exterior member 40 is sealed with the use of a thermal fusion bonding method or the like. As a result, since the wound body is impregnated with the electrolytic solution, the wound electrode body 30 is fabricated, and the wound electrode body 30 is sealed inside the exterior member 40. In this case, the adhesive film 41 is inserted between the positive electrode lead 31 and the exterior member 40, and the adhesive film 41 is inserted between the negative electrode lead 32 and the exterior member 40.

Thus, a laminated film type secondary battery is completed.

In a case where a gel electrolyte layer is used, an electrolytic solution, a polymer compound, an organic solvent, and the like are mixed to prepare a precursor solution. Then, the precursor solution is applied to a surface of the positive electrode 33, and then the precursor solution is dried to form the electrolyte layer. Further, the precursor solution is applied to the negative electrode 34, and then the precursor solution is dried to form the electrolyte layer. In a case where the wound body is fabricated after the process, the positive electrode 33 having the electrolyte layer formed thereon and the negative electrode 34 having the electrolyte layer formed thereon are stacked with the separator 35 interposed therebetween, and then the positive electrode 33, the negative electrode 34, the separator 35, and the electrolyte layer are wound.

[Action and Effects]

According to the laminated film type lithium ion secondary battery, the electrolytic solution has a configuration similar to that of the electrolytic solution of the present technology. Accordingly, as described above, the generation of gas resulting from the decomposition reaction of the electrolytic solution is suppressed while sufficiently advancing the charge and discharge reaction using the electrolyte salt. Therefore, even if the secondary battery is repeatedly used, the discharged capacity is less likely to decrease and the secondary battery is less likely to swell, whereby excellent battery characteristics can be obtained.

Particularly, in the laminated film type secondary battery fabricated by using the film-like exterior member 40 having flexibility, the above-described swollenness due to the generation of gas tends to become obvious. Therefore, the swollenness of the secondary battery can be effectively suppressed by utilizing the advantages based on the configuration of the electrolytic solution described above.

The other action and effects of the laminated film type lithium ion secondary battery are similar to the action and effects of the electrolytic solution of the present technology.

<3. Application of Secondary Battery>

Subsequently, application examples of the above-described secondary battery will be described.

The application of the secondary battery is not particularly limited, as long as the secondary battery is applied to machines, devices, instruments, apparatuses, systems, and the like (a collective entity of, for example, a plurality of devices) that can use the secondary battery as a driving power supply, a power storage source for reserve of power, or the like. The secondary battery used as a power supply may be a main power supply or an auxiliary power supply. The main power supply is a power supply that is used preferentially, regardless of the presence or absence of other power supplies. The auxiliary power supply may be, for example, a power supply which is used instead of the main power supply, or a power supply which is switched from the main power supply, if necessary. In a case where the secondary battery is used as the auxiliary power supply, the kind of the main power supply is not limited to the secondary battery.

Here are applications of the secondary battery, for example: electronic devices (including portable electronic devices) such as a video camera, a digital still camera, a mobile phone, a laptop personal computer, a cordless telephone, a headphone stereo, a portable radio, a portable television, and a portable information terminal; a mobile lifestyle appliance such as an electric shaver; a storage device such as a backup power supply and a memory card; a power tool such as an electric drill and an electric saw; a battery pack mounted on a laptop personal computer or the like as a detachable power supply; a medical electronic device such as a pacemaker and a hearing aid; an electric vehicle such as an electric car (including a hybrid car); and a power storage system such as a domestic battery system for accumulation of electric power for, for example, emergency. As a matter of course, the secondary battery may be employed for an application other than the applications mentioned above.

In particular, it is effective to apply the secondary battery to the battery pack, the electric vehicle, the power storage system, the power tool, the electronic device, or the like. This is because, since these applications require excellent battery characteristics, the use of the secondary battery according to the present technology can improve the performance effectively. The battery pack is a power supply that uses the secondary battery. As will be described later, this battery pack may use a unit cell or an assembled battery. The electric vehicle is a vehicle that operates (travels) with the secondary battery as a driving power supply, and may be a vehicle (a hybrid car or the like) provided with a driving source other than the secondary battery as mentioned above. The power storage system is a system that uses the secondary battery as a power storage source. For example, for a household power storage system, electric power is accumulated in the secondary battery that is the power storage source, thus making it possible to use home electric appliances and the like with the use of the accumulated electric power. The power tool is a tool which makes a movable section (such as a drill) movable with the secondary battery as a driving power supply. The electronic device is a device that performs various functions with the secondary battery as a driving power supply (a power supply source).

Hereinafter, some application examples of the secondary battery will be specifically described. The configuration of each application example described below is just considered by way of example, and the configuration of the application example can be thus changed appropriately.

<3-1. Battery Pack (Unit Cell)>

Figure 3:
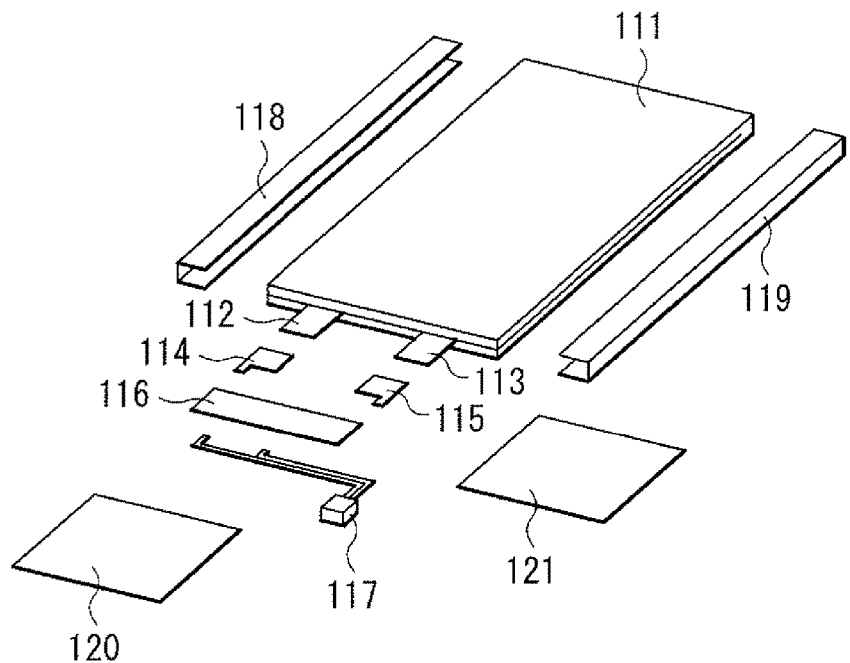
FIG. 3 is a perspective view illustrating a configuration of an application example (a battery pack: unit cell) of a secondary battery.
Figure 4:
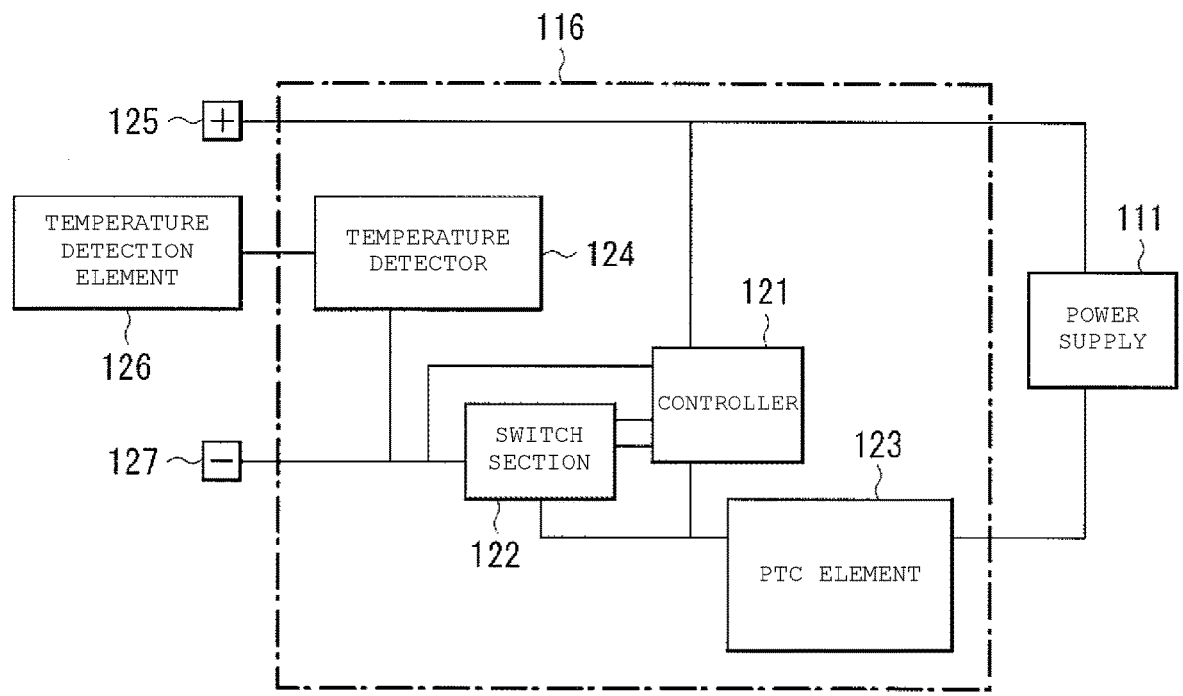
FIG. 4 is a block diagram illustrating the configuration of the battery pack illustrated in FIG. 3.

FIG. 3 illustrates a perspective configuration of a battery pack that uses a unit cell. FIG. 4 illustrates a block configuration of the battery pack illustrated in FIG. 3. It is to be noted that FIG. 3 shows the battery pack disassembled.

The battery pack described herein is a simplified battery pack (a so-called soft pack) that uses one secondary battery according to the present technology, and is mounted in, for example, an electronic device typified by a smart phone. This battery pack includes, for example, a power supply 111 that is a laminated film type secondary battery, and a circuit board 116 connected to the power supply 111, as illustrated in FIG. 3. A positive electrode lead 112 and a negative electrode lead 113 are attached to the power supply 111.

A pair of adhesive tapes 118 and 119 is attached to both side surfaces of the power supply 111. The circuit board 116 has a protection circuit (PCM: Protection Circuit Module) formed. The circuit board 116 is connected to the positive electrode 112 via a tab 114, and connected to the negative electrode lead 113 via a tab 115. Further, the circuit board 116 is connected to a lead wire 117 provided with a connector for external connection. In a state in which the circuit board 116 is connected to the power supply 111, the circuit board 116 is protected by a label 120 and an insulating sheet 121. The label 120 is adhered to fix, for example, the circuit board 116 and the insulating sheet 121.

Furthermore, for example, the battery pack includes the power supply 111 and the circuit board 116 as illustrated in FIG. 4. The circuit board 116 includes, for example, a controller 121, a switch section 122, a PTC element 123, and a temperature detector 124. The power supply 111 is connectable to outside via a positive electrode terminal 125 and a negative electrode terminal 127, and thus the power supply 111 is charged and discharged via the positive electrode terminal 125 and the negative electrode terminal 127. The temperature detector 124 detects the temperature with the use of a temperature detection terminal (a so-called T terminal) 126.

The controller 121 controls the operation of the whole battery pack (including a usage state of the power supply 111). The controller 121 includes, for example, a central processing unit (CPU) and a memory.

For example, when a battery voltage reaches an overcharge detection voltage, the controller 121 disconnects the switch section 122, thereby preventing any charging current from flowing through a current path of the power supply 111. Further, for example, when a large current flows during charging, the controller 121 disconnects the switch section 122, thereby shutting off the charging current.

Meanwhile, for example, when the battery voltage reaches the overdischarge detection voltage, the controller 121 disconnects the switch section 122, thereby preventing any discharging current from flowing through the current path of the power supply 111. Further, for example, when a large current flows during discharging, the controller 121 disconnects the switch section 122, thereby shutting off the discharging current.

The overcharge detection voltage is, for example, 4.2 V±0.05 V, and the overdischarge detection voltage is, for example, 2.4 V±0.1 V.

The switch section 122 switches the usage state of the power supply 111 (that is, whether there is a connection between the power supply 111 and an external device) in response to an instruction from the controller 121. The switch section 122 includes, for example, a charge control switch and a discharge control switch. The charge control switch and the discharge control switch each are, for example, a semiconductor switch such as a field effect transistor using a metal oxide semiconductor (MOSFET). The charge current and the discharge current are detected, for example, on the basis of ON resistance of the switch section 122.

The temperature detector 124 measures the temperature of the power supply 111, and outputs the temperature measurement result to the controller 121. The temperature detector 124 includes, for example, a temperature detection element such as a thermistor. The result of the temperature measured by the temperature detector 124 is used, in a case where the controller 121 performs charge and discharge control at the time of abnormal heat generation, in a case where the controller 121 performs correction processing at the time of calculating remaining capacity, and the like.

It is to be noted that the circuit board 116 does not necessarily include the PTC element 123. In this case, a PTC element may be separately attached to the circuit board 116.

<3-2. Battery Pack (Assembled Battery)>

Figure 5:
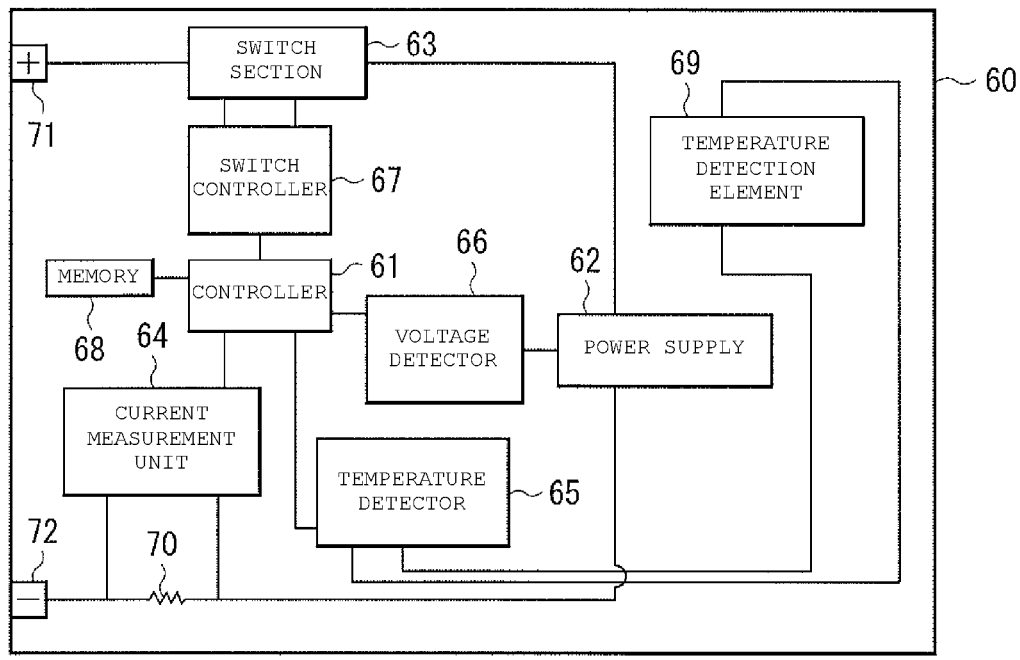
FIG. 5 is a block diagram illustrating a configuration of an application example (a battery pack: assembled battery) of a secondary battery.

FIG. 5 illustrates a block configuration of a battery pack that uses an assembled battery.

For example, the battery pack includes a controller 61, a power supply 62, a switch section 63, a current measurement unit 64, a temperature detector 65, a voltage detector 66, a switch controller 67, a memory 68, a temperature detection element 69, a current detection resistor 70, a positive electrode terminal 71, and a negative electrode terminal 72 inside a housing 60. The housing 60 includes, for example, a plastic material.

The controller 61 controls the operation of the whole battery pack (including a usage state of the power supply 62). The controller 61 includes, for example, a CPU. The power supply 62 is an assembled battery including two or more secondary batteries according to the present technology. The two or more secondary batteries may be connected in series, in parallel, or in series-parallel combination. To give an example, the power supply 62 includes six secondary batteries in which two sets of series-connected three batteries are connected in parallel to each other.

The switch section 63 switches the usage state of the power supply 62 (that is, whether there is a connection between the power supply 62 and an external device) in response to an instruction from the controller 61. The switch section 63 includes, for example, a charge control switch, a discharge control switch, a charging diode, and a discharging diode. The charge control switch and the discharge control switch each are, for example, a semiconductor switch such as a field effect transistor using a metal oxide semiconductor (MOSFET).

The current measurement unit 64 measures a current with the use of the current detection resistor 70, and outputs a current measurement result to the controller 61. The temperature detector 65 measures a temperature with the use of the temperature detection element 69, and outputs a temperature measurement result to the controller 61. The temperature measurement result is used, for example, in a case where the controller 61 performs charge and discharge control at the time of abnormal heat generation and in a case where the controller 61 performs correction processing at the time of calculating remaining capacity. The voltage detector 66 measures voltages of the secondary batteries in the power supply 62, to the controller 61, performs analog-to-digital conversion on the measured voltage, and supplies the result to the controller 61.

The switch controller 67 controls the operation of the switch section 63 in response to signals input from each of the current measurement unit 64 and the voltage detector 66.

For example, when a battery voltage reaches an overcharge detection voltage, the switch controller 67 disconnects the switch section 63 (the charge control switch), thereby preventing any charging current from flowing through a current path of the power supply 62. Thus, only discharge is allowed via the discharging diode in the power supply 62. For example, when a large current flows during charging, the switch controller 67 shuts off the charging current.

Further, for example, when the battery voltage reaches the overdischarge detection voltage, the switch controller 67 disconnects the switch section 63 (the discharge control switch), thereby preventing any discharging current from flowing through the current path of the power supply 62. Thus, only charge is allowed via the charging diode in the power supply 62. For example, when a large current flows during discharging, the switch controller 67 shuts off the discharging current.

The overcharge detection voltage is, for example, 4.2 V±0.05 V, and the overdischarge detection voltage is, for example, 2.4 V±0.1 V.

The memory 68 includes, for example, an EEPROM that is a non-volatile memory. The memory 68 stores, for example, numerical values calculated by the controller 61, and information of the secondary battery measured in a manufacturing process (for example, internal resistance in an initial state). Further, storing the full charge capacity of the secondary battery in the memory 68 makes it possible for the controller 61 to grasp information such as the remaining capacity.

The temperature detection element 69 measures a temperature of the power supply 62, and outputs a temperature measurement result to the controller 61. The temperature detection element 69 includes, for example, a thermistor.

Each of the positive electrode terminal 71 and the negative electrode terminal 72 is a terminal connected to an external device (for example, a laptop personal computer) operated with the use of the battery pack or an external device (for example, a charger) used for charging the battery pack, or the like. The power supply 62 is charged and discharged via the positive electrode terminal 71 and the negative electrode terminal 72.

<3-3. Electric Vehicle>

Figure 6:
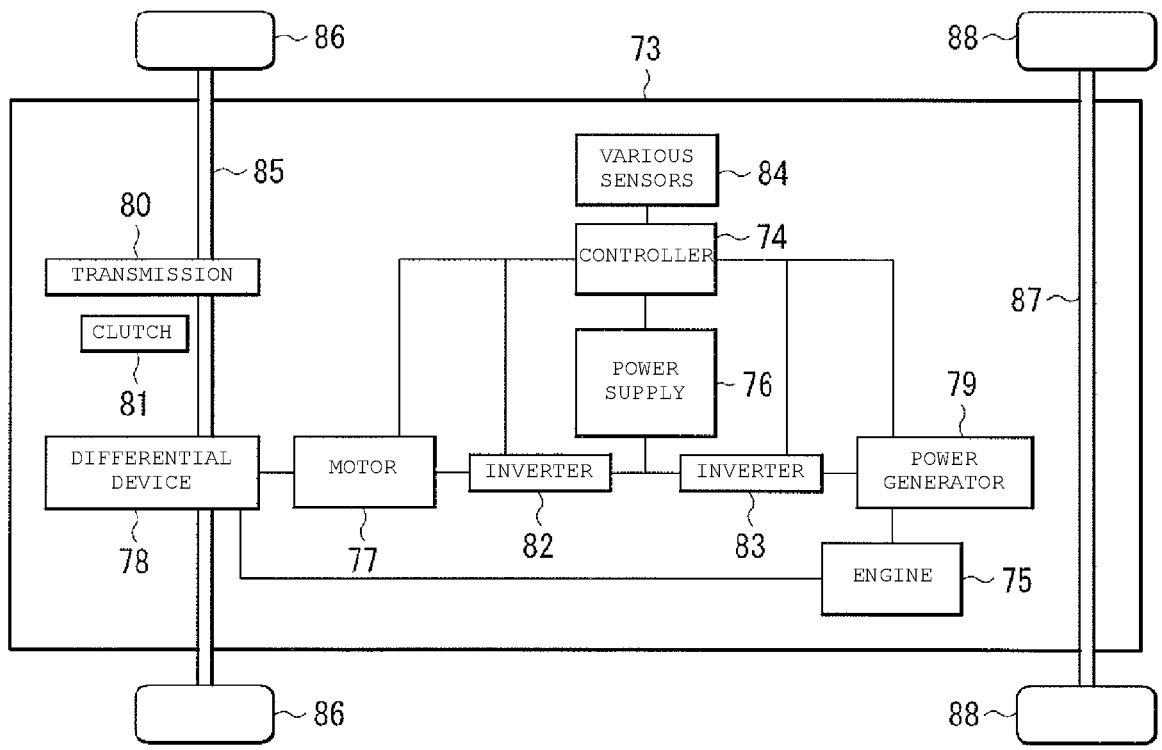
FIG. 6 is a block diagram illustrating a configuration of an application example (an electric vehicle) of a secondary battery.

FIG. 6 illustrates a block configuration of a hybrid car as an example of an electric vehicle.

The electric vehicle includes, for example, a controller 74, an engine 75, a power supply 76, a motor 77 for driving, a differential device 78, a power generator 79, a transmission 80, a clutch 81, an inverter 82, an inverter 83, and various sensors 84 inside a housing 73 made of metal. In addition, the electric vehicle includes, for example, a front-wheel drive shaft 85, front wheels 86 that are connected to the differential device 78 and the transmission 80, a rear-wheel drive shaft 87, and rear wheels 88.

The electric vehicle can travel, for example, with any one of the engine 75 and the motor 77 as a driving source. The engine 75 is a main power source, for example, a gasoline engine. In a case where the engine 75 is used as a power source, the driving force (torque) of the engine 75 is transmitted to the front wheels 86 or the rear wheels 88 via, for example, the differential device 78, the transmission 80, and the clutch 81 which are driving units. Further, the torque of the engine 75 is transmitted to the power generator 79, the power generator 79 thus generates alternating-current power by the use of the torque, and the alternating-current power is converted to direct-current power via the inverter 83, and the converted direct-current power is accumulated in the power supply 76. Meanwhile, in a case where the motor 77 that is a converter is used as the power source, the electric power (direct-current power) supplied from the power supply 76 is converted to alternating-current power via the inverter 82, and the motor 77 is thus driven by the use of the alternating-current power. The driving force (torque) converted from the electric power by the motor 77 is transmitted to the front wheels 86 and the rear wheels 88 via, for example, the differential device 78, the transmission 80, and the clutch 81 which are driving units.

The electric vehicle may be configured such that when the electric vehicle is decelerated via a braking mechanism, the resistance force at the time of deceleration is transmitted as a torque to the motor 77, and the motor 77 thus generates alternating-current power by the use of the torque. It is preferable that the alternating-current power be converted to direct-current power via the inverter 82, and the direct-current regenerative power be accumulated in the power supply 76.

The controller 74 controls the operation of the whole electric vehicle. The controller 74 includes, for example, a CPU. The power supply 76 includes one or two or more secondary batteries according to the present technology. The power supply 76 is connected to an external power supply, and the power supply 76 is allowed to accumulate electric power by receiving supply of electric power from the external power supply. The various sensors 84 are used, for example, for controlling a rotation speed of the engine 75, and controlling an opening level (a throttle opening level) of a throttle valve. The various sensors 84 include, for example, any one of, or two or more of a speed sensor, an acceleration sensor, and an engine speed sensor.

Although the case where the electric vehicle is a hybrid car has been given as an example, the electric vehicle may be a vehicle (electric car) that operates with the use of only the power supply 76 and the motor 77 without using the engine 75.

<3-4. Power Storage System>

Figure 7:
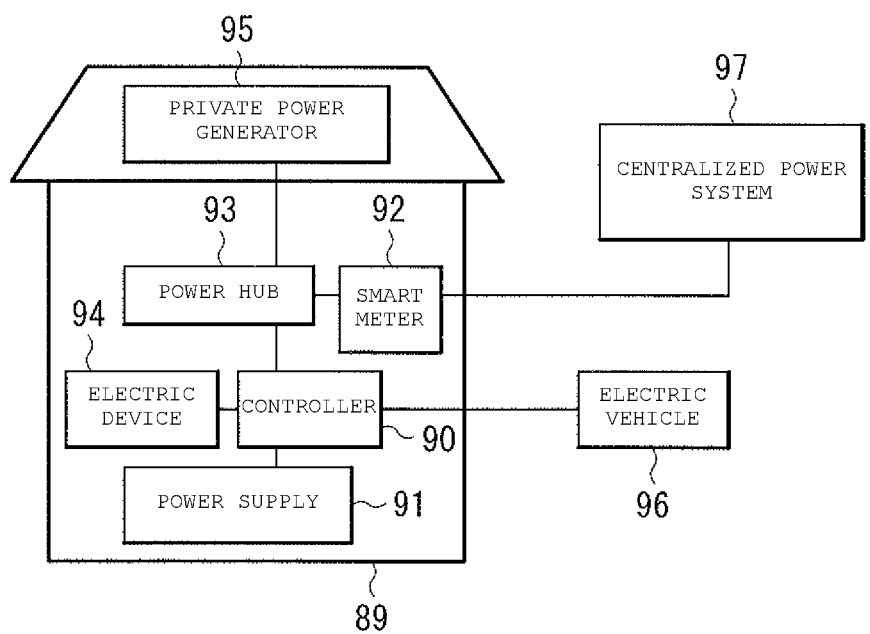
FIG. 7 is a block diagram illustrating a configuration of an application example (a power storage system) of a secondary battery.

FIG. 7 illustrates a block configuration of a power storage system.

The power storage system includes, for example, a controller 90, a power supply 91, a smart meter 92, and a power hub 93 inside a house 89 such as a general residence and a commercial building.

Here, the power supply 91 is connected to, for example, an electric device 94 installed inside the house 89, and is allowed to be connected to an electric vehicle 96 parked outside the house 89. Further, the power supply 91 is, for example, connected via the power hub 93 to a private power generator 95 installed in the house 89, and is allowed to be connected to an external centralized power system 97 via the smart meter 92 and the power hub 93.

The electric device 94 includes, for example, one or two or more home electric appliances, and examples of the home electric appliances include a refrigerator, an air conditioner, a television, and a water heater. The private power generator 95 includes, for example, any one of, or two or more of a solar power generator and a wind power generator. The electric vehicle 96 includes, for example, any one of, or two or more of an electric car, an electric bike, and a hybrid car. The centralized power system 97 includes, for example, any one of, or two or more of a thermal power plant, a nuclear power plant, a hydraulic power plant, and a wind power plant.

The controller 90 controls the operation of the whole power storage system (including a usage state of the power supply 91). The controller 90 includes, for example, a CPU. The power supply 91 includes one or two or more secondary batteries according to the present technology. The smart meter 92 is, for example, an electric power meter that is compatible with a network and is installed in the house 89 demanding electric power, and is communicable with an electric power supplier. Accordingly, the smart meter 92 controls the balance between demand and supply of electric power in the house 89 while communicating with the outside, thereby allowing highly efficient and stable supply of energy.

In this power storage system, for example, electric power is accumulated in the power supply 91 via the smart meter 92 and the power hub 93 from the centralized power system 97 that is an external power supply, and electric power is accumulated in the power supply 91 via the power hub 93 from the private power generator 95 that is an independent power supply. The electric power accumulated in the power supply 91 is supplied to the electric device 94 and the electric vehicle 96 in response to an instruction from the controller 90, this allows the electric device 94 to be operable, and allows the electric vehicle 96 to be chargeable. More specifically, the power storage system is a system that allows electric power to be accumulated and supplied in the house 89 with the use of the power supply 91.

It is possible to use the electric power accumulated in the power supply 91, if necessary. Hence, for example, it is possible to accumulate electric power in the power supply 91 from the centralized power system 97 in the middle of night when an electric rate is inexpensive, and it is possible to use the electric power accumulated in the power supply 91 during daytime hours when the electric rate is expensive.

The power storage system described above may be installed for each household (one family unit), or may be installed for a plurality of households (a plurality of family units).

<3-5. Power Tool>

Figure 8:
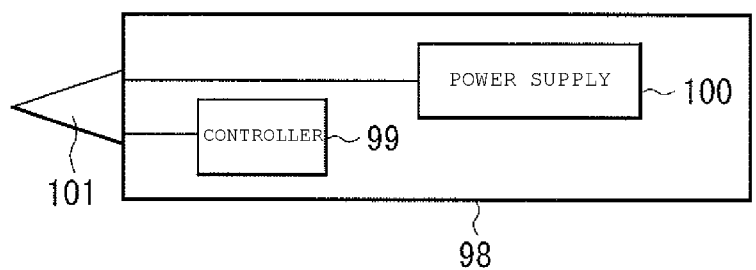
FIG. 8 is a block diagram illustrating a configuration of an application example (a power tool) of a secondary battery.

FIG. 8 illustrates a block configuration of a power tool.

The power tool described herein is, for example, an electric drill. The power tool includes, for example, a controller 99 and a power supply 100 inside a tool body 98. For example, a drill section 101 as a movable section is operably (rotatably) attached to the tool body 98.

The tool body 98 includes, for example, a plastic material. The controller 99 controls the operation of the whole power tool (including a usage state of the power supply 100). The controller 99 includes, for example, a CPU. The power supply 100 includes one or two or more secondary batteries according to the present technology. The controller 99 supplies electric power from the power supply 100 to the drill section 101 in response to an operation of an operation switch.

EXAMPLES

Examples of the present technology will be described.

Experimental Examples 1-1 to 1-37

Laminated film type lithium ion secondary batteries illustrated in FIGS. 1 and 2 were fabricated in accordance with the following procedure.

In a case where the positive electrode 33 was fabricated, 94 parts by mass of a positive electrode active material ($LiNi_{0.82}Co_{0.15}Al_{0.03}O_2$, median diameter D50=13 μm), 3 parts by mass of a positive electrode binder (polyvinylidene fluoride), and 3 parts by mass of a positive electrode conductive agent (acetylene black) were mixed to obtain a positive electrode mixture. Then, the positive electrode mixture was put in an organic solvent (N-methyl-2-pyrrolidone), the organic solvent was then stirred, thereby preparing a paste-like positive electrode mixture slurry. Then, the positive electrode mixture slurry was applied to both sides of the positive electrode current collector 33A (20 μm thick belt-like aluminum foil) with the use of a coating device, and the positive electrode mixture slurry was then dried to form the positive electrode active material layer 33B. Finally, the positive electrode active material layer 33B was subjected to compression-molding with the use of a roll press machine.

In a case where the negative electrode 34 was fabricated, 95 parts by mass of a negative electrode active material (graphite, median diameter D50=20 μm) and 5 parts by mass of a negative electrode binder (polyvinylidene fluoride) were first mixed to obtain a negative electrode mixture. After that, the negative electrode mixture was put in an organic solvent (N-methyl-2-pyrrolidone), the organic solvent was then stirred, thereby preparing a paste-like negative electrode mixture slurry. Thereafter, the negative electrode mixture slurry was applied to both sides of the negative electrode current collector 34A (15 μm-thick belt-like copper foil) with the use of a coating device, and the negative electrode mixture slurry was then dried to form the negative electrode active material layer 34B. Finally, the negative electrode active material layer 34B was subjected to compression-molding with the use of a roll press machine.

In the case of preparing an electrolytic solution, an electrolyte salt ($LiPF_6$) was added to a solvent and the solvent was stirred, and then each of the sulfone compounds was added to the solvent and the solvent was stirred. Tables 1 to 3 show the kind of solvent, the solvent composition (content of each component in the solvent: wt %), the content of electrolyte salt in the electrolytic solution (mol/kg), the molar ratio M2/M1, the kind of each of the sulfone compounds, and the content (weight) of each of the sulfone compounds in the electrolytic solution. In this case, the molar ratio M2/M1 was varied by changing the additive amount of the electrolyte salt (the content of the electrolyte salt in the electrolytic solution) and the content of ethylene carbonate in the solvent.

Here, five nonaqueous solvents were used as the solvents. Specifically, cyclic carbonate esters such as ethylene carbonate (EC) and propylene carbonate (PC), chain carbonate esters such as diethyl carbonate (DEC) and ethyl methyl carbonate (EMC), and a chain carboxylate ester such as propyl propionate (PRP) were used.

Further, the compound represented by the formula (1-1) as the first sulfone compound, the compound represented by the formula (2-1) as the second sulfone compound, and the compound represented by the formula (3-1) as the third sulfone compound were used as the sulfone compounds. If necessary, the sulfone compounds were not used for the comparison.

In the case of assembling the secondary battery, first, the positive electrode lead 31 made of aluminum was welded to the positive electrode current collector 33A, and the negative electrode lead 32 made of nickel was welded to the negative electrode current collector 34A. Then, a stacked body was obtained by stacking the positive electrode 33 and the negative electrode 34 with the separator 35 (a microporous polyethylene stretched film having a thickness of 20 μm) interposed therebetween. After that, the stacked body was wound in a longitudinal direction, and then a protective tape was adhered to the outermost peripheral part of the stacked body to fabricate a wound body. Thereafter, the exterior member 40 was folded so as to sandwich the wound body, and the outer periphery edges of three sides of the exterior member 40 were heat-sealed. The exterior member 40 is an aluminum laminated film in which a 25-μm-thick nylon film, a 40-μm-thick aluminum foil, and a 30-μm-thick polypropylene film are laminated in this order from the outside. In this case, the adhesive film 41 was inserted between the positive electrode lead 31 and the exterior member 40, and the adhesive film 41 was inserted between the negative electrode lead 32 and the exterior member 40. Finally, the electrolytic solution was injected into the inside of the exterior member 40 to impregnate the wound body with the electrolytic solution, and then the outer periphery edges of the remaining one side of the exterior member 40 were heat-sealed in a reduced-pressure environment. As a result, the wound electrode body 30 was fabricated, and the wound electrode body 30 was enclosed in the inside of the exterior member 40, and thus a laminated film type lithium ion secondary battery was completed.

In order to evaluate the battery characteristics of the secondary battery, the swollenness characteristics, storage characteristics, and cycle characteristics of the secondary battery were examined, and the results shown in Tables 1 to 3 were obtained.

In the case of examining the swollenness characteristics, the swollenness ratio (%) was determined by performing a storage test. Specifically, the secondary battery was first charged and discharged in an ambient temperature environment (temperature=25° C.) in order to stabilize the state of the secondary battery. After that, the secondary battery was charged in the same environment, and the thickness of the charged secondary battery (thickness before storage) was measured. Thereafter, the charged secondary battery was stored (storage time=6 months) in a high temperature environment (temperature=70° C.), and then the thickness of the charged secondary battery in an ambient temperature environment (temperature=25° C.) (thickness after storage) was measured. Finally, the swollenness ratio (%) (=[(thickness after storage-thickness before storage)/thickness before storage]×100) was calculated.

When the secondary battery was charged, charge was performed at a constant current of 0.2 C until the voltage reached 4.3 V, and thereafter, charge was further performed at a constant voltage of 4.3 V until the current reached 0.05 C. When the secondary battery was discharged, discharge was performed at a constant current of 0.2 C until the voltage reached 2.5V. "0.2 C" refers to a current value at which the battery capacity (theoretical capacity) is completely discharged in 5 hours, and "0.05 C" refers to a current value at which the battery capacity is completely discharged in 20 hours.

In the case of examining the storage characteristics, the storage retention ratio (%) was determined when the above-described storage test was performed. Specifically, the secondary battery was first charged and discharged in an ambient temperature environment (temperature=25° C.) in order to stabilize the state of the secondary battery. After that, the secondary battery was charged and discharged in the same environment, thereby measuring the discharged capacity (discharged capacity before storage). Thereafter, the secondary battery was stored (storage time=6 months) in a high temperature environment (temperature=70° C.), and then the secondary battery was charged and discharged in an ambient temperature environment (temperature=25° C.) thereby measuring the discharged capacity (discharged capacity after storage). Finally, the storage retention ratio (%) (=(discharged capacity after storage/discharged capacity before storage)×100) was calculated.

The charge and discharge conditions were similar to those in the case of examining the swollenness characteristics.

In a case where the cycle characteristics were examined, a cycle test was performed to calculate the cycle retention ratio (%). Specifically, the secondary battery was first charged and discharged (for one cycle) in an ambient temperature environment (temperature=25° C.) in order to stabilize the state of the secondary battery. After that, one cycle of charge and discharge was performed on the secondary battery in the same environment (temperature=25° C.), thereby measuring the 2nd-cycle discharged capacity. Thereafter, the secondary battery was repeatedly charged and discharged until the number of cycles reached 1000 cycles in the same environment, thereby measuring the 1000th-cycle discharged capacity. Finally, a cycle retention ratio (%)=(1000th-cycle discharged capacity/2nd-cycle discharged capacity)×100 was calculated.

When the secondary battery was charged, charge was performed at a constant current of 1 C until the voltage reached 4.3 V, and thereafter, charge was further performed at a constant voltage of 4.3 V until the current reached 0.05 C. When the secondary battery was discharged, discharge was performed at a constant current of 5 C until the voltage reached 2.5V. "1 C" refers to a current value at which the battery capacity (theoretical capacity) is completely discharged in 1 hour, and "5 C" refers to a current value at which the battery capacity is completely discharged in 0.2 hours.

TABLE 1

| | Positive electrode active material: $LiNi_{0.82}Co_{0.15}Al_{0.03}O_2$ | | | | | | | | | | | | |
|---|---|---|---|---|---|---|---|---|---|---|---|---|---|
| | Solvent composition (content: wt %) | | | | | Electrolyte salt | | Molar ratio | Sulfone compounds | | Swollenness ratio | Storage retention ratio | Cycle retention ratio |
| Experimental Examples | EC | PC | EMC | DEC | PRP | Kind | Content (mol/kg) | M2/M1 | Kind | Content (wt %) | (%) | (%) | (%) |
| 1-1 | 25 | 15 | 30 | 30 | — | $LiPF_6$ | 1.0 | 2.4 | Formula (1-1) | 0.01 | 9.0 | 81 | 76 |
| 1-2 | 25 | 15 | 30 | 30 | — | $LiPF_6$ | 1.0 | 2.4 | Formula (1-1) | 0.1 | 7.9 | 82 | 79 |
| 1-3 | 25 | 15 | 30 | 30 | — | $LiPF_6$ | 1.0 | 2.4 | Formula (1-1) | 1 | 3.0 | 86 | 87 |
| 1-4 | 25 | 15 | 30 | 30 | — | $LiPF_6$ | 1.0 | 2.4 | Formula (1-1) | 5 | 2.6 | 85 | 83 |
| 1-5 | 25 | 15 | 30 | 30 | — | $LiPF_6$ | 1.0 | 2.4 | Formula (1-1) | 10 | 2.0 | 83 | 76 |
| 1-6 | 25 | 15 | 30 | 30 | — | $LiPF_6$ | 1.0 | 2.4 | Formula (2-1) | 0.01 | 8.8 | 83 | 77 |
| 1-7 | 25 | 15 | 30 | 30 | — | $LiPF_6$ | 1.0 | 2.4 | Formula (2-1) | 0.1 | 4.4 | 86 | 83 |
| 1-8 | 25 | 15 | 30 | 30 | — | $LiPF_6$ | 1.0 | 2.4 | Formula (2-1) | 1 | 2.2 | 88 | 90 |
| 1-9 | 25 | 15 | 30 | 30 | — | $LiPF_6$ | 1.0 | 2.4 | Formula (2-1) | 5 | 1.8 | 84 | 83 |
| 1-10 | 25 | 15 | 30 | 30 | — | $LiPF_6$ | 1.0 | 2.4 | Formula (2-1) | 10 | 0.9 | 83 | 81 |
| 1-11 | 25 | 15 | 30 | 30 | — | $LiPF_6$ | 1.0 | 2.4 | Formula (3-1) | 0.01 | 9.2 | 82 | 78 |
| 1-12 | 25 | 15 | 30 | 30 | — | $LiPF_6$ | 1.0 | 2.4 | Formula (3-1) | 0.1 | 6.7 | 85 | 83 |
| 1-13 | 25 | 15 | 30 | 30 | — | $LiPF_6$ | 1.0 | 2.4 | Formula (3-1) | 1 | 2.1 | 86 | 89 |
| 1-14 | 25 | 15 | 30 | 30 | — | $LiPF_6$ | 1.0 | 2.4 | Formula (3-1) | 5 | 1.9 | 84 | 83 |
| 1-15 | 25 | 15 | 30 | 30 | — | $LiPF_6$ | 1.0 | 2.4 | Formula (3-1) | 10 | 1.0 | 82 | 79 |

TABLE 2

Positive electrode active material: $LiNi_{0.82}Co_{0.15}Al_{0.03}O_2$

| Experimental Examples | Solvent composition (content: wt %) | | | | | Electrolyte salt | Content (mol/kg) | Molar ratio M2/M1 | Sulfone compounds | Content (wt %) | Swollenness ratio (%) | Storage retention ratio (%) | Cycle retention ratio (%) |
|---|---|---|---|---|---|---|---|---|---|---|---|---|---|
| | EC | PC | EMC | DEC | PRP | Kind | | | Kind | | | | |
| 1-16 | 25 | 15 | 30 | 30 | — | LiPF$_6$ | 1.0 | 2.4 | Formula (1-1) + Formula (2-1) | 5 + 5 | 1.4 | 80 | 79 |
| 1-17 | 25 | 15 | 30 | 30 | — | LiPF$_6$ | 1.0 | 2.4 | Formula (1-1) + Formula (3-1) | 5 + 5 | 1.1 | 81 | 80 |
| 1-18 | 25 | 15 | 30 | — | 30 | LiPF$_6$ | 1.0 | 2.4 | Formula (2-1) | 1 | 1.6 | 89 | 80 |
| 1-19 | 10 | 30 | 30 | 30 | — | LiPF$_6$ | 1.0 | 0.97 | Formula (2-1) | 1 | 1.0 | 82 | 77 |
| 1-20 | 25 | 15 | 30 | 30 | — | LiPF$_6$ | 2.0 | 1.0 | Formula (2-1) | 1 | 1.2 | 82 | 77 |
| 1-21 | 10 | 30 | 30 | 30 | — | LiPF$_6$ | 2.0 | 0.4 | Formula (2-1) | 1 | 0.4 | 81 | 79 |
| 1-22 | 30 | 10 | 30 | 30 | — | LiPF$_6$ | 1.2 | 2.3 | Formula (2-1) | 1 | 2.0 | 83 | 82 |
| 1-23 | 30 | — | 40 | 30 | — | LiPF$_6$ | 1.2 | 2.3 | Formula (2-1) | 1 | 3.2 | 84 | 84 |
| 1-24 | 20 | 20 | 30 | 30 | — | LiPF$_6$ | 0.8 | 2.4 | Formula (2-1) | 1 | 0.8 | 81 | 76 |
| 1-25 | 25 | 15 | 30 | 30 | — | LiPF$_6$ | 1.0 | 2.4 | — | — | 12 | 80 | 75 |
| 1-26 | 30 | 10 | 30 | 30 | — | LiPF$_6$ | 1.0 | 2.8 | — | — | 20 | 79 | 70 |
| 1-27 | 30 | 10 | 30 | 30 | — | LiPF$_6$ | 1.0 | 2.8 | Formula (1-1) | 1 | 11 | 78 | 71 |
| 1-28 | 30 | 10 | 30 | 30 | — | LiPF$_6$ | 1.0 | 2.8 | Formula (2-1) | 1 | 9.1 | 78 | 73 |
| 1-29 | 30 | 10 | 30 | 30 | — | LiPF$_6$ | 1.0 | 2.8 | Formula (3-1) | 1 | 10 | 77 | 73 |

TABLE 3

Positive electrode active material: $LiNi_{0.82}Co_{0.15}Al_{0.03}O_2$

| Experimental Examples | Solvent composition (content: wt %) | | | | | Electrolyte salt | Content (mol/kg) | Molar ratio M2/M1 | Sulfone compounds | Content (wt %) | Swollenness ratio (%) | Storage retention ratio (%) | Cycle retention ratio (%) |
|---|---|---|---|---|---|---|---|---|---|---|---|---|---|
| | EC | PC | EMC | DEC | PRP | Kind | | | Kind | | | | |
| 1-30 | 25 | 15 | 30 | 30 | — | LiPF$_6$ | 0.7 | 3.6 | — | — | 35 | 75 | 51 |
| 1-31 | 25 | 15 | 30 | 30 | — | LiPF$_6$ | 0.7 | 3.6 | Formula (1-1) | 1 | 21 | 74 | 54 |
| 1-32 | 25 | 15 | 30 | 30 | — | LiPF$_6$ | 0.7 | 3.6 | Formula (2-1) | 1 | 17 | 73 | 58 |
| 1-33 | 25 | 15 | 30 | 30 | — | LiPF$_6$ | 0.7 | 3.6 | Formula (3-1) | 1 | 17 | 74 | 56 |
| 1-34 | 7.5 | 30 | 32.5 | 30 | — | LiPF$_6$ | 2.0 | 0.3 | — | — | 2.1 | 86 | 58 |
| 1-35 | 7.5 | 30 | 32.5 | 30 | — | LiPF$_6$ | 2.0 | 0.3 | Formula (1-1) | 1 | 1.8 | 87 | 68 |
| 1-36 | 7.5 | 30 | 32.5 | 30 | — | LiPF$_6$ | 2.0 | 0.3 | Formula (2-1) | 1 | 0.9 | 89 | 61 |
| 1-37 | 7.5 | 30 | 32.5 | 30 | — | LiPF$_6$ | 2.0 | 0.3 | Formula (3-1) | 1 | 1.1 | 89 | 64 |

In a case where the solvent contained ethylene carbonate, each of the swollenness ratio, the storage retention ratio, and the cycle retention ratio varied depending on the content of ethylene carbonate, the content of electrolyte salt, the molar ratio M2/M1, the presence or absence of the sulfone compounds, and the like.

Specifically, in a case where the three conditions (content of ethylene carbonate: 10 wt % to 30 wt %, content of electrolyte salt: 0.8 mol/kg to 2.0 mol/kg, molar ratio M2/M1:0.4 to 2.4) were simultaneously satisfied, when the electrolytic solution contained the sulfone compounds (Experimental Examples 1-1 to 1-24), each of the storage retention ratio and the cycle retention ratio increased sufficiently while the swollenness ratio decreased sufficiently, as compared with the case where the electrolytic solution did not contain the sulfone compounds and the case where the three conditions were not simultaneously satisfied (Experimental Examples 1-25 to 1-37).

Particularly, in a case where the three conditions were satisfied and the electrolytic solution contained the sulfone compounds, when the content of the sulfone compounds in the electrolytic solution was from 0.01 wt % to 10 wt %, the swollenness ratio was sufficiently decreased, and the storage retention ratio and the cycle retention ratio were increased sufficiently.

Further, when the solvent contained propylene carbonate, the swollenness ratio was further reduced while maintaining a high storage retention ratio and a high cycle retention ratio, as compared with a case where the solvent did not contain propylene carbonate.

Experimental Examples 2-1 to 2-37

As shown in Tables 4 to 6, secondary batteries were fabricated by a procedure similar to those in Experimental Examples 1-1 to 1-37 except that the kind of positive electrode active material was changed, and the battery characteristics (swollenness characteristics, storage characteristics, and cycle characteristics) of each of the secondary batteries were examined.

In the case of fabricating the positive electrode 33, first, the procedure similar to the above-described procedure was performed, except that 91 parts by mass of a positive electrode active material (LiCoO$_2$), 3 parts by mass of a positive electrode binder (polyvinylidene fluoride), and 6 parts by mass of a positive electrode conductive agent (graphite) were mixed.

In the case of examining each of the swollenness characteristics, storage characteristics, and cycle characteristics, the charge and discharge conditions were the same except that the charge voltage was changed to 4.4 V and the discharge voltage was changed to 3.0 V.

TABLE 4

Positive electrode active material: LiCoO$_2$

| Experimental Examples | Solvent composition (content: wt %) | | | | | Electrolyte salt | | Molar ratio | Sulfone compounds | | Swollenness ratio | Storage retention ratio | Cycle retention ratio |
|---|---|---|---|---|---|---|---|---|---|---|---|---|---|
| | EC | PC | EMC | DEC | PRP | Kind | Content (mol/kg) | M2/M1 | Kind | Content (wt %) | (%) | (%) | (%) |
| 2-1 | 25 | 15 | 30 | 30 | — | LiPF$_6$ | 1.0 | 2.4 | Formula (1-1) | 0.01 | 9.9 | 75 | 83 |
| 2-2 | 25 | 15 | 30 | 30 | — | LiPF$_6$ | 1.0 | 2.4 | Formula (1-1) | 0.1 | 7.5 | 76 | 84 |
| 2-3 | 25 | 15 | 30 | 30 | — | LiPF$_6$ | 1.0 | 2.4 | Formula (1-1) | 1 | 4.1 | 79 | 89 |
| 2-4 | 25 | 15 | 30 | 30 | — | LiPF$_6$ | 1.0 | 2.4 | Formula (1-1) | 5 | 3.1 | 77 | 87 |
| 2-5 | 25 | 15 | 30 | 30 | — | LiPF$_6$ | 1.0 | 2.4 | Formula (1-1) | 10 | 2.4 | 75 | 84 |
| 2-6 | 25 | 15 | 30 | 30 | — | LiPF$_6$ | 1.0 | 2.4 | Formula (2-1) | 0.01 | 9.8 | 75 | 84 |
| 2-7 | 25 | 15 | 30 | 30 | — | LiPF$_6$ | 1.0 | 2.4 | Formula (2-1) | 0.1 | 4.9 | 76 | 86 |
| 2-8 | 25 | 15 | 30 | 30 | — | LiPF$_6$ | 1.0 | 2.4 | Formula (2-1) | 1 | 3.8 | 79 | 91 |
| 2-9 | 25 | 15 | 30 | 30 | — | LiPF$_6$ | 1.0 | 2.4 | Formula (2-1) | 5 | 2.9 | 76 | 87 |
| 2-10 | 25 | 15 | 30 | 30 | — | LiPF$_6$ | 1.0 | 2.4 | Formula (2-1) | 10 | 1.9 | 75 | 85 |
| 2-11 | 25 | 15 | 30 | 30 | — | LiPF$_6$ | 1.0 | 2.4 | Formula (3-1) | 0.01 | 9.1 | 75 | 84 |
| 2-12 | 25 | 15 | 30 | 30 | — | LiPF$_6$ | 1.0 | 2.4 | Formula (3-1) | 0.1 | 7.0 | 75 | 86 |
| 2-13 | 25 | 15 | 30 | 30 | — | LiPF$_6$ | 1.0 | 2.4 | Formula (3-1) | 1 | 4.0 | 78 | 89 |
| 2-14 | 25 | 15 | 30 | 30 | — | LiPF$_6$ | 1.0 | 2.4 | Formula (3-1) | 5 | 2.8 | 77 | 86 |
| 2-15 | 25 | 15 | 30 | 30 | — | LiPF$_6$ | 1.0 | 2.4 | Formula (3-1) | 10 | 2.1 | 75 | 83 |

TABLE 5

Positive electrode active material: LiCoO$_2$

| Experimental Examples | Solvent composition (content: wt %) | | | | | Electrolyte salt | | Molar ratio | Sulfone compounds | | Swollenness ratio | Storage retention ratio | Cycle retention ratio |
|---|---|---|---|---|---|---|---|---|---|---|---|---|---|
| | EC | PC | EMC | DEC | PRP | Kind | Content (mol/kg) | M2/M1 | Kind | Content (wt %) | (%) | (%) | (%) |
| 2-16 | 25 | 15 | 30 | 30 | — | LiPF$_6$ | 1.0 | 2.4 | Formula (1-1) + Formula (2-1) | 5 + 5 | 1.8 | 75 | 84 |
| 2-17 | 25 | 15 | 30 | 30 | — | LiPF$_6$ | 1.0 | 2.4 | Formula (1-2) + Formula (3-1) | 5 + 5 | 1.9 | 75 | 85 |
| 2-18 | 25 | 15 | 30 | — | 30 | LiPF$_6$ | 1.0 | 2.4 | Formula (2-1) | 1 | 3.3 | 78 | 87 |
| 2-19 | 10 | 30 | 30 | 30 | — | LiPF$_6$ | 1.0 | 0.97 | Formula (2-1) | 1 | 1.6 | 80 | 85 |
| 2-20 | 25 | 15 | 30 | 30 | — | LiPF$_6$ | 2.0 | 1.0 | Formula (2-1) | 1 | 2.2 | 75 | 84 |
| 2-21 | 10 | 30 | 30 | 30 | — | LiPF$_6$ | 2.0 | 0.4 | Formula (2-1) | 1 | 1.4 | 73 | 83 |
| 2-22 | 30 | 10 | 30 | 30 | — | LiPF$_6$ | 1.2 | 2.3 | Formula (2-1) | 1 | 2.9 | 76 | 84 |
| 2-23 | 30 | — | 40 | 30 | — | LiPF$_6$ | 1.2 | 2.3 | Formula (2-1) | 1 | 4.8 | 79 | 87 |
| 2-24 | 20 | 20 | 30 | 30 | — | LiPF$_6$ | 0.8 | 2.4 | Formula (2-1) | 1 | 1.3 | 76 | 83 |
| 2-25 | 25 | 15 | 30 | 30 | — | LiPF$_6$ | 1.0 | 2.4 | — | — | 15 | 74 | 82 |
| 2-26 | 30 | 10 | 30 | 30 | — | LiPF$_6$ | 1.0 | 2.8 | — | — | 21 | 70 | 74 |
| 2-27 | 30 | 10 | 30 | 30 | — | LiPF$_6$ | 1.0 | 2.8 | Formula (1-1) | 1 | 18 | 69 | 75 |
| 2-28 | 30 | 10 | 30 | 30 | — | LiPF$_6$ | 1.0 | 2.8 | Formula (2-1) | 1 | 13 | 68 | 77 |
| 2-29 | 30 | 10 | 30 | 30 | — | LiPF$_6$ | 1.0 | 2.8 | Formula (3-1) | 1 | 15 | 66 | 76 |

TABLE 6

| | Solvent composition (content: wt %) | | | | | Electrolyte salt | | Molar ratio | Sulfone compounds | | Swollenness ratio | Storage retention ratio | Cycle retention ratio |
|---|---|---|---|---|---|---|---|---|---|---|---|---|---|
| Experimental Examples | EC | PC | EMC | DEC | PRP | Kind | Content (mol/kg) | M2/M1 | Kind | Content (wt %) | (%) | (%) | (%) |
| 2-30 | 25 | 15 | 30 | 30 | — | LiPF$_6$ | 0.7 | 3.6 | — | — | 40 | 65 | 59 |
| 2-31 | 25 | 15 | 30 | 30 | — | LiPF$_6$ | 0.7 | 3.6 | Formula (1-1) | 1 | 27 | 65 | 64 |
| 2-32 | 25 | 15 | 30 | 30 | — | LiPF$_6$ | 0.7 | 3.6 | Formula (2-1) | 1 | 22 | 63 | 68 |
| 2-33 | 25 | 15 | 30 | 30 | — | LiPF$_6$ | 0.7 | 3.6 | Formula (3-1) | 1 | 23 | 63 | 65 |
| 2-34 | 7.5 | 30 | 32.5 | 30 | — | LiPF$_6$ | 2.0 | 0.3 | — | — | 10 | 78 | 71 |
| 2-35 | 7.5 | 30 | 32.5 | 30 | — | LiPF$_6$ | 2.0 | 0.3 | Formula (1-1) | 1 | 6.3 | 79 | 74 |
| 2-36 | 7.5 | 30 | 32.5 | 30 | — | LiPF$_6$ | 2.0 | 0.3 | Formula (2-1) | 1 | 5.2 | 79 | 71 |
| 2-37 | 7.5 | 30 | 32.5 | 30 | — | LiPF$_6$ | 2.0 | 0.3 | Formula (3-1) | 1 | 5.1 | 79 | 70 |

Positive electrode active material: LiCoO$_2$

Even if the kind of positive electrode active material was changed (Tables 4 to 6), the results similar to the results shown in Tables 1 to 3 were obtained.

That is, in a case where the three conditions (content of ethylene carbonate: 10 wt % to 30 wt %, content of electrolyte salt: 0.8 mol/kg to 2.0 mol/kg, molar ratio M2/M1:0.4 to 2.4) were satisfied, when the electrolytic solution contained the sulfone compounds (Examples 2-1 to 2-24), each of the storage retention ratio and the cycle retention ratio increased sufficiently while the swollenness ratio decreased sufficiently, as compared with the case where the electrolytic solution did not contain the sulfone compounds and the case where the three conditions were not simultaneously satisfied (Experimental Examples 2-25 to 2-37).

The results in Tables 1 to 6 showed that the solvent contained ethylene carbonate, and the three conditions described above were simultaneously satisfied with respect to the content of ethylene carbonate in the solvent, the content of electrolyte salt in the electrolytic solution, and the molar ratio M2/M1, and the electrolyte contained the sulfone compounds, whereby the swollenness characteristics, storage characteristics, and cycle characteristics were all improved. Therefore, excellent battery characteristics were obtained in the secondary battery.

The present technology has been described above with reference to an embodiment and examples, but the present technology is not limited to the aspects described in the embodiment and the examples, and various modifications are possible.

Specifically, although the case where the battery element has a wound structure has been described, the structure of the battery element in the secondary battery of the present technology is not particularly limited. Specifically, the battery element may have any other structure such as a laminated structure.

Note that the effects described in the present specification are illustrative and non-limiting, and the present technology may have effects other than those described in the present specification.

The present technology may have the following configurations.

(1)
A secondary battery including:
a positive electrode;
a negative electrode; and
an electrolytic solution
in which
(A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3).

[Chem. 16]

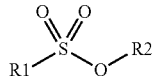

(1)

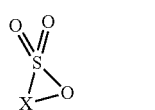

(2)

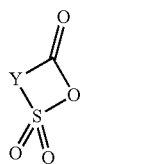

(3)

(where each of R1 and R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, provided that at least one of R1 and R2 is any one of the monovalent unsaturated hydrocarbon group and the monovalent binding group, and each of X and Y is a divalent unsaturated hydrocarbon group.)

(2)

The secondary battery according to (1), in which the monovalent saturated hydrocarbon group is any one of an alkyl group, a cycloalkyl group, and a monovalent group in which two or more of the alkyl group and the cycloalkyl group are bound, the monovalent unsaturated hydrocarbon group is any one of an alkenyl group, an alkynyl group, an aryl group, and a monovalent group in which two or more of the alkenyl group, the alkynyl group, and the aryl group are bound, and the divalent unsaturated hydrocarbon group is any one of an alkenylene group, an alkynylene group, an arylene group, and a group in which two or more of the alkenylene group, the alkynylene group, and the arylene group are bound.

(3)

The secondary battery according to (1) or (2), in which the sulfone compound represented by the formula (1) includes at least one of compounds represented by formulas (1-1) to (1-4), the sulfone compound represented by the formula (2) includes at least one of compounds represented by formulas (2-1) to (2-3), and the sulfone compound represented by the formula (3) includes at least one of compounds represented by formulas (3-1) to (3-3).

[Chem.17]

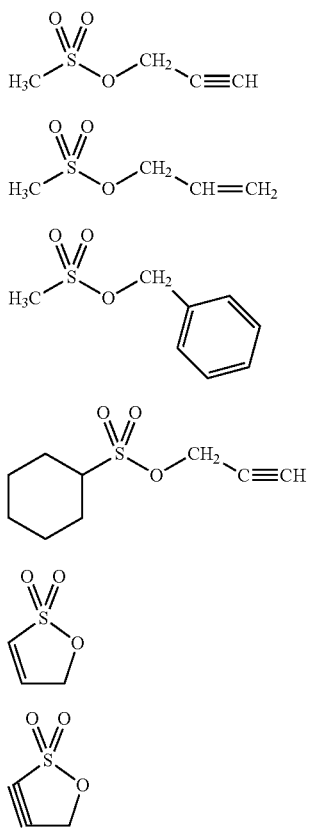

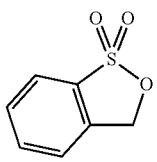

(2-3)

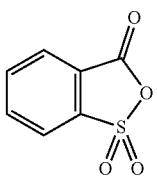

(3-1)

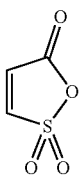

(3-2)

(3-3)

(4)

The secondary battery according to any one of claims (1) to (3), in which a content of the sulfone compound in the electrolytic solution is from 0.01 wt % to 10 wt % both inclusive.

(5)

The secondary battery according to any one of (1) to (4), in which the solvent contains a cyclic carbonate ester and at least one of a chain carbonate ester and a chain carboxylate ester, the cyclic carbonate ester includes the ethylene carbonate, the chain carbonate ester includes at least one of diethyl carbonate and ethyl methyl carbonate, and the chain carboxylate ester includes at least one of ethyl propionate and propyl propionate.

(6)

The secondary battery according to (5), in which the cyclic carbonate ester further includes propylene carbonate, and a content of the propylene carbonate in the solvent is 30 wt % or less.

(7)

The secondary battery according to any one of (1) to (6), in which the electrolyte salt includes at least one of lithium salts.

(8)

The secondary battery according to (1) to (7), in which the positive electrode, the negative electrode, and the electrolytic solution are each housed inside a film-like exterior member.

(9)

The secondary battery according to any one of (1) to (8), in which the secondary battery is a lithium ion secondary battery.

(10)

An electrolytic solution for a secondary battery, in which (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3).

[Chem. 18]

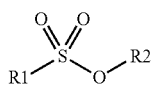
(1)

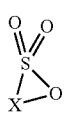
(2)

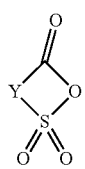
(3)

(where each of R1 and R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, provided that at least one of R1 and R2 is any one of the monovalent unsaturated hydrocarbon group and the monovalent binding group, and each of X and Y is a divalent unsaturated hydrocarbon group.)

(11)

A battery pack including:

the secondary battery according to any one of (1) to (9);

a controller that controls an operation of the secondary battery; and a switch section that switches the operation of the secondary battery in response to an instruction from the controller.

(12)

An electric vehicle including:

the secondary battery according to any one of (1) to (9);

a converter that converts electric power supplied from the secondary battery into a driving force;

a driving unit that drives in response to the driving force; and a controller that controls an operation of the secondary battery.

(13)

A power storage system including:

the secondary battery according to any one of (1) to (9);

at least one electric device that has a supply of electric power from the secondary battery; and a controller that controls the supply of the electric power to the electric device from the secondary battery.

(14)

A power tool including:

the secondary battery according to any one of (1) to (9); and a movable section that is supplied with electric power from the secondary battery.

(15)

An electronic device including the secondary battery according to any one of (1) to (9) as a power supply source.

This application claims the priority based on Japanese Patent Application No. 2017-021046 filed on Feb. 8, 2017 in the Japanese Patent Office, the entire contents of which are incorporated herein by reference.

One skilled in the art may conceive of various modifications, combinations, subcombinations, and modifications depending on design requirements and other factors, which are understood to be included within the spirit of the appended claims and the scope of equivalents thereof.

The invention claimed is:

1. A secondary battery comprising:

a positive electrode;

a negative electrode; and an electrolytic solution wherein (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3):

[Chem. 1]

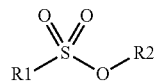
(1)

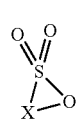
(2)

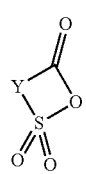
(3)

where R1 is any one of an alkyl group, a cycloalkyl group, and a monovalent group in which two or more of the alkyl group and the cycloalkyl group are bound, R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynylene group or arylene group.

2. The secondary battery according to claim 1, wherein
the monovalent saturated hydrocarbon group is any one of an alkyl group, a cycloalkyl group, and a monovalent group in which two or more of the alkyl group and the cycloalkyl group are bound,
the monovalent unsaturated hydrocarbon group is any one of an alkenyl group, an alkynyl group, an aryl group, and a monovalent group in which two or more of the alkenyl group, the alkynyl group, and the aryl group are bound, and
the divalent unsaturated hydrocarbon group is any one of an alkenylene group, an alkynylene group, an arylene group, and a group in which two or more of the alkenylene group, the alkynylene group, and the arylene group are bound.

3. The secondary battery according to claim 1, wherein
the sulfone compound represented by the formula (1) includes at least one of compounds represented by formulas (1-1) to (1-4),
the sulfone compound represented by the formula (2) includes at least one of compounds represented by formulas (2-2) to (2-3), and
the sulfone compound represented by the formula (3) includes at least one of compounds represented by formulas (3-1) to (3-3):

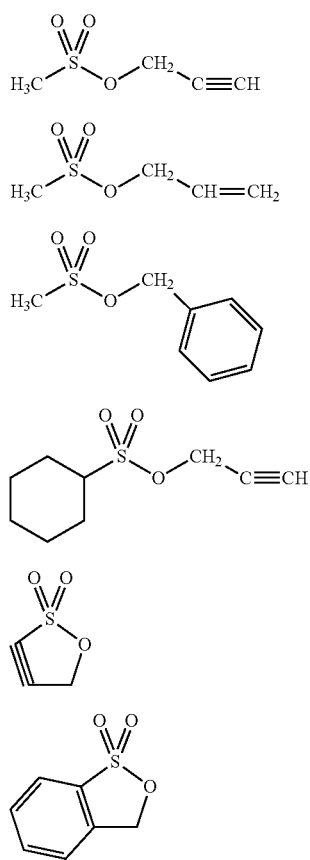

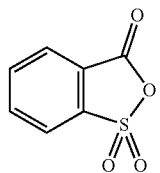

(3-1)

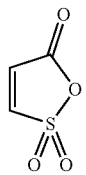

(3-2)

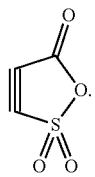

(3-3)

4. The secondary battery according to claim 1, wherein a content of the sulfone compound in the electrolytic solution is from 0.01 wt % to 10 wt % both inclusive.

5. The secondary battery according to claim 1, wherein
the solvent contains a cyclic carbonate ester and at least one of a chain carbonate ester and a chain carboxylate ester,
the cyclic carbonate ester includes the ethylene carbonate,
the chain carbonate ester includes at least one of diethyl carbonate and ethyl methyl carbonate, and
the chain carboxylate ester includes at least one of ethyl propionate and propyl propionate.

6. The secondary battery according to claim 5, wherein
the cyclic carbonate ester further includes propylene carbonate, and
a content of the propylene carbonate in the solvent is 30 wt % or less.

7. The secondary battery according to claim 1, wherein the
electrolyte salt includes at least one of lithium salts.

8. The secondary battery according to claim 1, wherein the
positive electrode, the negative electrode, and the electrolytic solution are each housed inside a film-like exterior member.

9. The secondary battery according to claim 1, wherein the
secondary battery is a lithium ion secondary battery.

10. An electrolytic solution for a secondary battery, wherein
the electrolytic solution contains a solvent and an electrolyte salt, the solvent containing ethylene carbonate,
a content of the electrolyte salt is from 0.8 mol/kg to 2.0 mol/kg both inclusive,
a content of the ethylene carbonate in the solvent is from 10 wt % to 30 wt % both inclusive,
a ratio M2/M1 of a number M2 of moles of the ethylene carbonate to a number M1 of moles of the electrolyte salt is from 0.4 to 2.4 both inclusive, and the electrolytic solution contains at least one of sulfone compounds represented by formulas (1), (2), and (3):

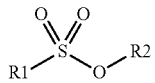 (1)

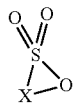 (2)

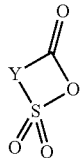 (3)

where R1 is any one of an alkyl group, a cycloalkyl group, and a monovalent group in which two or more of the alkyl group and the cycloalkyl group are bound, R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynlene group or an arylene group.

11. A battery pack comprising:
a secondary battery;
a controller that controls an operation of the secondary battery; and
a switch section that switches the operation of the secondary battery in response to an instruction of the controller;
the secondary battery including:
a positive electrode,
a negative electrode, and
an electrolytic solution,
wherein (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3):

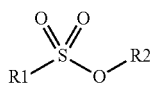 (1)

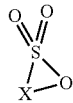 (2)

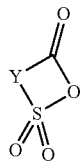 (3)

where R1 is any one of an alkyl group, a cycloalkyl group, and a monovalent group in which two or more of the alkyl group and the cycloalkyl group are bound, R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynlene group or an arylene group.

12. An electric vehicle comprising:
a secondary battery;
a converter that converts electric power supplied from the secondary battery into a driving force;
a driving unit that drives in response to the driving force; and
a controller that controls an operation of the secondary battery,
the secondary battery including:
a positive electrode,
a negative electrode, and
an electrolytic solution,
wherein (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3):

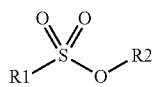 (1)

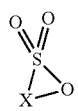 (2)

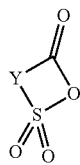 (3)

where R1 is any one of an alkyl group, a cycloalkyl group, and a monovalent group in which two or more of the alkyl group and the cycloalkyl group are bound, and R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynlene group or an arylene group.

13. A power storage system comprising:
a secondary battery;
at least one electric device that has a supply of electric power from the secondary battery; and
a controller that controls the supply of the electric power to the electric device from the secondary battery;
the secondary battery including:
a positive electrode,
a negative electrode, and
an electrolytic solution,
wherein (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3):

[Chem. 6]

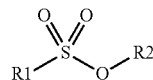
(1)

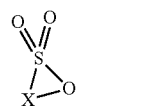
(2)

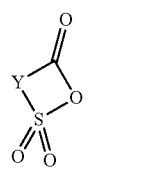
(3)

where R1 is any one of an alkyl group, a cycloalkyl group, and a monovalent group in which two or more of the alkyl group and the cycloalkyl group are bound, and R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynlene group or an arylene group.

14. A power tool comprising:
a secondary battery; and
a movable section that is supplied with electric power from the secondary battery;
the secondary battery including:
a positive electrode,
a negative electrode, and
an electrolytic solution
wherein (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3):

[Chem. 7]

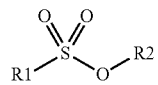
(1)

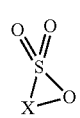
(2)

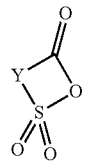
(3)

where R1 is any one of an alkyl group, a cycloalkyl group, and a monovalent group in which two or more of the alkyl group and the cycloalkyl group are bound, R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynlene group or an arylene group.

15. An electronic device comprising a secondary battery as
a power supply source,
the secondary battery including:
a positive electrode,
a negative electrode, and
an electrolytic solution
wherein (A) the electrolytic solution contains a solvent and an electrolyte salt, the solvent containing ethylene carbonate, (B) a content of the electrolyte salt is from 0.8 mol/kg to 2.0 mol/kg both inclusive, (C) a content of the ethylene carbonate in the solvent is from 10 wt % to 30 wt % both inclusive, (D) a ratio M2/M1 of a number M2 of moles of the ethylene carbonate to a number M1 of moles of the electrolyte salt is from 0.4 to 2.4 both inclusive, and (E) the electrolytic solution contains at least one of sulfone compounds represented by formulas (1), (2), and (3):

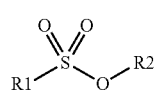
(1)

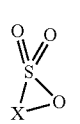
(2)

-continued

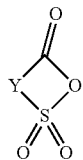

(3)

where R1 is any one of an alkyl group, a cycloalkyl group, and a monovalent group in which two or more of the alkyl group and the cycloalkyl group are bound, R2 is any one of a monovalent saturated hydrocarbon group, a monovalent unsaturated hydrocarbon group, and a monovalent binding group in which two or more of the monovalent saturated hydrocarbon group and the monovalent unsaturated hydrocarbon group are bound, Y is a divalent unsaturated hydrocarbon group, and X is an alkynlene group or an arylene group.

* * * * *